(12) United States Patent
Greenfield

(10) Patent No.: US 12,102,751 B2
(45) Date of Patent: Oct. 1, 2024

(54) POSITIVE PRESSURE INHALER FOR DELIVERY OF INHALABLE MEDICATION AND METHODS FOR USE

(71) Applicant: Jon Greenfield, Los Angeles, CA (US)

(72) Inventor: Jon Greenfield, Los Angeles, CA (US)

(*) Notice: Subject to any disclaimer, the term of this patent is extended or adjusted under 35 U.S.C. 154(b) by 1202 days.

(21) Appl. No.: 16/852,204

(22) Filed: Apr. 17, 2020

(65) Prior Publication Data

US 2020/0330706 A1 Oct. 22, 2020

Related U.S. Application Data

(60) Provisional application No. 62/835,992, filed on Apr. 18, 2019.

(51) Int. Cl.
*A61M 15/00* (2006.01)
*A61M 11/00* (2006.01)
(Continued)

(52) U.S. Cl.
CPC ........ *A61M 15/009* (2013.01); *A61M 11/007* (2014.02); *A61M 11/02* (2013.01);
(Continued)

(58) Field of Classification Search
CPC .. A61M 15/009; A61M 11/007; A61M 11/02; A61M 15/0021; A61M 15/0065; A61M 15/0086; A61M 39/22; A61M 2039/248; A61M 2202/0208; A61M 2202/0241; A61M 2205/073; A61M 2205/3334; A61M 2205/3337; A61M 2205/581; A61M 2205/583; A61M 2205/8206; A61M 15/0088; A61M 11/042; A61M 2205/07; A61M 2205/3379; A61M 15/0003; A61M 15/06; A61M 15/0016; A61M 15/08; A61M 16/06; A61M 2209/02; A61M 2209/08; A61M 2202/048
See application file for complete search history.

(56) References Cited

U.S. PATENT DOCUMENTS 3,635,213 A * 1/1972 LaHay ................. A61B 5/4266
119/14.14
4,836,198 A 6/1989 Gates
(Continued)

FOREIGN PATENT DOCUMENTS

EP 3693044 A1 * 8/2020 .......... A61M 15/009
WO WO-9204066 A1 * 3/1992
(Continued)

OTHER PUBLICATIONS

International Search Report and Written Opinion mailed by PCT, ISA/US on Jul. 23, 2020 in the corresponding PCT application No. PCT/US2020/028872—20 pages.
(Continued)

*Primary Examiner* — LaToya M Louis
(74) *Attorney, Agent, or Firm* — Lapple Ubell IP Law, LLP; Matthew C. Lapple

(57) ABSTRACT

Embodiments disclosed herein include a positive pressure inhaler for delivery of aerosolized/vaporized medication to a patient's lungs under positive pressure and in a known volume of air, and methods of using the positive pressure inhaler for such delivery.

32 Claims, 28 Drawing Sheets

(51) Int. Cl.
   *A61M 11/02* (2006.01)
   *A61M 39/22* (2006.01)
   *A61M 39/24* (2006.01)
(52) U.S. Cl.
   CPC .... *A61M 15/0021* (2014.02); *A61M 15/0065* (2013.01); *A61M 15/0086* (2013.01); *A61M 39/22* (2013.01); *A61M 2039/248* (2013.01); *A61M 2202/0208* (2013.01); *A61M 2202/0241* (2013.01); *A61M 2205/073* (2013.01); *A61M 2205/3334* (2013.01); *A61M 2205/3337* (2013.01); *A61M 2205/581* (2013.01); *A61M 2205/583* (2013.01); *A61M 2205/8206* (2013.01)

(56) References Cited

U.S. PATENT DOCUMENTS

| | | | |
|---|---|---|---|
| 5,005,571 | A | 4/1991 | Dietz |
| 5,226,793 | A | 7/1993 | Stovall |
| 5,336,066 | A | 8/1994 | Myers et al. |
| 5,497,944 | A | 3/1996 | Weston et al. |
| 5,584,285 | A | 12/1996 | Salter et al. |
| 5,755,221 | A | 5/1998 | Bisgaard |
| 6,192,876 | B1 | 2/2001 | Denyer et al. |
| 6,223,746 | B1 | 5/2001 | Jewett et al. |
| 6,390,090 | B1 | 5/2002 | Piper |
| 6,702,997 | B2 | 3/2004 | Chaudry et al. |
| 6,904,908 | B2 | 6/2005 | Bruce et al. |
| 7,185,648 | B1 * | 3/2007 | Rand ............... B01F 33/452 128/200.23 |
| 7,201,165 | B2 | 4/2007 | Bruce et al. |
| 7,246,617 | B1 | 7/2007 | Harmer et al. |
| 9,272,103 | B2 | 3/2016 | Storz |
| 2002/0069869 | A1 * | 6/2002 | Farmer ............. A61M 15/0086 128/203.29 |
| 2003/0159694 | A1 | 8/2003 | McNaughton |
| 2003/0205229 | A1 * | 11/2003 | Crockford ............. A61P 11/06 128/200.23 |
| 2004/0000307 | A1 * | 1/2004 | Khan ................ A61M 15/0086 128/200.22 |
| 2005/0279349 | A1 | 12/2005 | Patton et al. |
| 2006/0062739 | A1 | 3/2006 | Hofmann et al. |
| 2008/0168987 | A1 | 7/2008 | Denny et al. |
| 2011/0168175 | A1 | 7/2011 | Dunne et al. |
| 2012/0010568 | A1 | 1/2012 | Smith |
| 2013/0269695 | A1 | 10/2013 | Brouet et al. |
| 2014/0352690 | A1 | 12/2014 | Kolb et al. |
| 2017/0127727 | A1 | 5/2017 | Davidson et al. |
| 2017/0307483 | A1 | 10/2017 | Farina et al. |
| 2017/0367406 | A1 | 12/2017 | Schuler et al. |
| 2018/0055091 | A1 * | 3/2018 | Trzecieski .......... A61M 15/009 |
| 2020/0078541 | A1 * | 3/2020 | Lewis ................ A61M 15/0083 |

FOREIGN PATENT DOCUMENTS

| | | | |
|---|---|---|---|
| WO | 9512428 | A1 | 5/1995 |
| WO | 2008049433 | A1 | 5/2008 |
| WO | 2015066256 | A1 | 5/2015 |

OTHER PUBLICATIONS

"The World Programmable Drug Delivery Inhalation Platform," Syqe Medical, https://www/syqemedical.com, Apr. 24, 2020—13 pages.
"A Retrospective Study of the Effectiveness of the AeroChamber Plus® Flow—Vu® Antistatic Valved Holding Chamber for Asthma Control," Pulmonary Therapy, vol. 3, Issue 2, pp. 283-296, Dec. 2017—22 pages.
Melissa E. Badowski,"A review of oral cannabinoids and medical marijuana for the treatment of chemotherapy-induced nausea and vomiting: a focus on pharmacokinetic variability and pharmacodynamics," Cancer Chemother Pharmacol, 80(3): 441-449, published online Aug. 5, 2017—17 pages.
Aerochamber Plus® Z Stat® AVHC, Medicines and Healthcare Products Regulatory Agency, Jul. 2008—7 pages.
Bruce K. Rubin, "Aerosol Medications for Treatment of Mucus Clearance Disorders," Respiratory Care, vol. 60, No. 6, www.rcjournal.com, Jun. 2015, pp. 825-832.
Michael W. Sims,"Aerosol Therapy for Obstructive Lung Diseases," Chest, 140(3): 781-788, Sep. 2011—22 pages.
Tim Op't Hott, et al.,"A Patient's Guide to Aerosol Medication Delivery 3rd edition," The American Association for Respiratory Care, 2017—55 pages.
AccuNeb® (albuterol sulfate) Inhalation Solution, Reference ID: 2912465, DEY, www.dey.com, Apr. 2006—17 pages.
Albuterol Sulfate, Ontology Summary from ChEBI, PubChem, Jan. 5, 2019 (Modify Date)—55 pages.
Kerstin Iffaland, et al., "An Update on Safety and Side Effects of Cannabidol: a review of clinical data and relevant animal studies," Cannabis Cannabinoid, Research: 2:1: 139-154, published online Jun. 1, 2017—27 pages.
Natascia Bruni, et al.,"Cannabinoid Delivery Systems for Pain and Inflammation Treatment," Molecules 2018, 23, 2478, www.mdpi.com/journal/molecules, published Sep. 27, 2018—25 pages.
Penny F. Whiting, Ph.D., et al., "Cannabinoids for Medical Use A Systematic Review and Meta—analysis," JAMA, 2015; 313(24): 2456-2473—35 pages.
Sarah K. Himes, et al., "Cannabinoids in Exhaled Breath following Controlled Administration of Smoked Cannabis," Clinical Chemistry 59:12(2013), pp. 1780-1789.
Jennifer Margham, et al.,"Chemical Composition of Aerosol from an E-Cigarette: A Quantitative Comparison with Cigarette Smoke," Chemical Research in Toxicology, Sep. 18, 2016, pp. 1662-1678.
Rebecca L. Hartman, et al.,"Controlled Cannabis Vaporizer Administration: Blood and Plasma Cannabinoids with and without Alcohol," Clinical Chemistry 61:6(2015), pp. 850-869.
Vincent Varlet, et al.,"Drug vaping applied to cannabis: Is "Cannavaping" a therapeutic alternative to marijuana?" Scientific Reports, vol. 6, Article No. 25599, Published May 26, 2016—35 page.
Franjo Grotenherman, "Harm Reduction Associated with Inhalation and Oral Administration of Cannabis and THC," Journal of Cannabis Therapeutics, vol. 1, No. 3/4, 2001, pp. 133-152.
"How to use a turbuhaler," Child and Adolescent Health Service—5 pages.
Kyle Merwin,"How to Use an Oil Cartridge Weed Vaporizer," Aug. 25, 2017—9 pages.
"How to use your Easyhaler inhaler,"—2 pages.
"Ideal Vaping Temperatures for Marijuana," Leaf Schience (leafscience.com), Leafly (leafly.com), https://emblemcannabis.com/turn-up-the-heat/,—5 pages.
Jeffry G. Weers, et al.,"Idealhalers Versus Realhalders: Is It Possible to Bypass Deposition in the Upper Respiratory Tract?" Journal of Aerosol Medicine and Pulmonary Drug Delivery Ahead of Print, published Dec. 6, 2018, https://doi.org/10.1089/jamp. 2018.1497, Published Online Dec. 6, 2018—1 page.
Sinthia Z. Bosnic-Anticevich, et al.,"Identifying Critical Errors Addressing Inhaler Technique in the Context of Asthma Management," Pulmonary Therapy, vol. 4, Issue 1, Jun. 2018—25 pages.
Mark L. Levy, et al.,"Inhaler technique facts and fantasies—A view from the Aerosol Drug Management Improvement Team (ADMIT)," npj Primary Care Respiratory Medicine, vol. 26, Article No. 16017, published Apr. 21, 2016—39 pages.
Julian L. Azorlosa, et al.,"Marijuana Smoking: Effects of Varying Puff Volume and Breathhold Duration," The Journal of Pharmacology and Experimental Therapeutics, vol. 272, No. 2, Oct. 7, 1994, pp. 560-569.
Christian Lanz, et al.,"Medicinal Cannabis In Vitro Validation of Vaporizers for the Smoke Free Inhalation of Cannabis," https://doi.org/10.1371/journal pone.0147286, Jan. 19, 2016—27 pages.
Caroline A. MacCallum, et al., "Practical considerations in medical cannabis administration and dosing," European Journal of Internal Medicine(2018)—8 pages.
Walter Vincken, et al.,"Spacer devices for inhaled thearapy: why use them, and how?," ERJ Open Research 2018 4: May 18, 2018—24 pages.

(56) References Cited

OTHER PUBLICATIONS

Giorgio Walter Canonica, MD., et al.,"Spiromax a New Dry Powder Inhaler Dose Consistency under Simulated Real-World Conditions," J. Aerosol Med Pulm Drug Deliv: Oct. 1, 2015: 28(5): 309-319—28 pages.
Staccato fentanyl controller and dose cartridge—1 page.
Mark Smiriotis,"The Best Portable Vaporizer," Grenco Science G Pen Elite, Apr. 20, 2018—40 pages.
Ed Oswald,"The best vaporizers of 2019," Emerging Tech., Jan. 6, 2019—11 pages.
Dr. Stephen Newman, "The Challenge of Delivering Inhaled Drugs to the Lung," The DDL Lecture 2016—30 pages.
"The Pari Inhalation Device—A Short Terminology Guide," Pari Service—4 pages.
Stephen P. Newman, Ph.D.,"Principles of Metered-Dose Inhaler Design," Respiratory Care, vol. 50, No. 9, Sep. 2005, pp. 1177-1190.
AEROBIKA®OPEP Aerosol Delivery Respiratory Management, monagham, http://www.monaghanmed.com/Aerobika-OPEP, Apr. 24, 2020—4 pages.
Aerosol Medication—8 pages.
Aaron Cadena, "What is CBD Bioavailability and Why Does it Matter?," Jun. 26, 2018—7 pages.
Nadia Kounang, CNN,"What you need to know about fentanyl," Nov. 5, 2018—3 pages.
The extended European Search Report issued by European Patent Office on Jan. 2, 2023 and Supplementary European Search Report issued on Dec. 19, 2022—9 pages in total.

\* cited by examiner

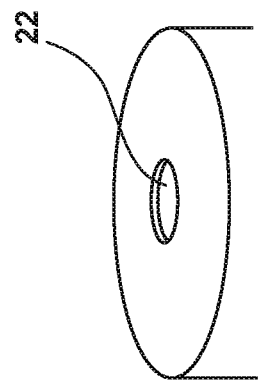
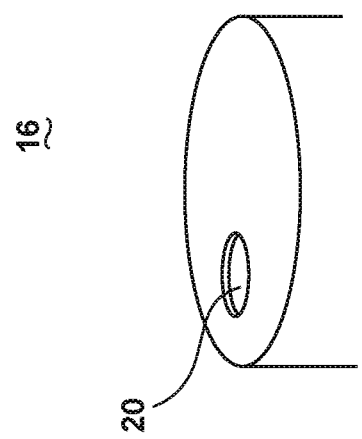
FIG. 11

POSITIVE PRESSURE INHALER FOR DELIVERY OF INHALABLE MEDICATION AND METHODS FOR USE

FIELD OF THE DISCLOSURE

The embodiments of the described invention relate generally to a treatment device for delivery of inhalable medication and methods of use.

BACKGROUND

The delivery of any medication to patients can be problematic. The delivery of medication to patients can generally be by any one of a number of delivery routes, including (a) intravenous; (b) respiratory; (c) oral; (d) rectal; (e) transdermal; (f) buccal/oral mucosal; and (g) sublingual. In most cases, the most effective administration of medication is via intravenous injection. The intravenous route requires an IV for the administration of medication. Medication delivery is exact and immediate. The second most effective method of administration of medication is respiratory delivery. Advantages normally include: (a) providing local action within the respiratory tract; (b) providing rapid drug action; (c) providing a reduced overall systemic dose; (e) allowing for a reduction in systemic side-effects; (f) use as an alternative route to avoid drug interaction when two or more medications are used concurrently; (g) reduction of extracellular enzyme levels compared to GI tract delivery, due to the large alveolar surface area for drug uptake; (h) reduction of drug detoxification due to first pass hepatic metabolism by the absorbed drug; and (i) it offers the potential for pulmonary administration of systemically active materials.

On the other hand, disadvantages of respiratory delivery include: (a) a short duration of activity due to rapid removal of the drug; (b) the requirement of frequent dosing for sustained effect depending on the drug half-life and the method of detoxification; and (c) irritation to the lungs and possible long term damage to the lungs.

Bioavailability is a measure of the amount of medication that is available to obtain a desired effect. The medication is absorbed into a living system and then takes effect.

The most common inhaled medications are those used for the treatment of asthma. Inhaled aerosol therapy is the most commonly used method of treatment for asthma and similar respiratory problems. The most common device for such treatment in a hospital setting is a common nebulizer, and the most common device for such treatment outside of the hospital is a pressurized Metered Dose Inhaler ("pMDI"). (See FIG. 1 PRIOR ART)

Known for many years, the only meaningful improvement in the pMDI delivery system has been the introduction of a respiratory holding chamber in which the medication is sprayed into the holding chamber first. The patient then inhales from the respiratory holding chamber. (See FIG. 2 PRIOR ART)

The current state of the art for respiratory delivery is the respiratory holding chamber/inhalation chamber as shown in FIG. 2 PRIOR ART. A meaningful drawback is that use of this inhalation chamber device still requires the patient to inhale. As such, the patient has to learn how to control his respiration, and the dosage of the medication and the concentration of the medication are dependent upon the patient's expertise in using the chamber, e.g., variability in inhalation volume, speed and depth result in variations in medication dosage and delivery and exposure to the number of alveoli able to uptake such medication. There are significant disadvantages to the use of the chamber. If the patient has a poor inspiratory effort the medication flow is altered. If the patient is small the volume inhaled will be less than if the patient is large. While some prior art chambers make noises if the inspiration is not at the correct inspiratory rate, this is a poor indicator and can be ignored by patients.

A recent study (2018) reviewed the effectiveness of available inhalation chambers. "Inhaled aerosol therapy remains the cornerstone of effective treatment of asthma and COPD. While the medications themselves have not changed dramatically over the past decades, the delivery devices have changed. Technology has allowed the development of more efficient and user-friendly inhalers. Nevertheless, incorrect inhaler technique remains a significant barrier to many users of inhaled medications. The most common errors reported for the use of pMDIs are lack of coordination between actuation and inhalation, halting inhalation when the cool spray hits the back of the throat, not holding the breath long enough (>5 seconds) after inhalation, no exhalation prior to actuation, and not shaking the suspension prior to use. Valved holding chambers ("VHCs") confer distinct advantages to the first two challenges. VHCs allow users to approach inhalation of aerosol medication as a two-step process: actuation into the chamber, followed by inhalation from the VHC mouthpiece. Technology has also allowed the development of more effective VHCs. There are now antistatic chambers, better valves, more effective facemasks, and other innovations that help deliver the intended dose of medication. VHCs have been proven to improve pMDI medication delivery to the lungs, reduce oropharyngeal deposition, and help users overcome challenges in coordinating pMDI actuation with inhalation. Moreover, newer VHCs with multiple advances (antistatic chamber and inhalation indicators) have been reported to improve asthma control, reduce the rate of exacerbations, and improve quality of life. VHCs are not all the same, and also are not interchangeable. Ongoing education is critical to ensure that users are consistently able to use their inhalers." *Optimizing the Delivery of Inhaled Medication for Respiratory Patients: The Role of Valved Holding Chambers*, Can Respir J. 2018; 2018: 5076259. Published online 2018 Apr. 4. doi: 10.1155/2018/5076259.

In another study, (*Marijuana Smoking: Effects of Varying Puff Volume and Breathholding*, JPET 272:560-569, 1995) subjects were subjected to computer training in order to achieve controlled inhalation volume. The study found that "As expected, varying marijuana dose by manipulating puff volume produced linear changes in CO boost, plasma THC levels, and subjective reports." Furthermore, there was a cumulative effect of puff volume. Total puff volume could be equated with the amount of THC delivered into the patient. Since THC is a medication, this study indicates that the delivery of aerosolized or vaporized medication is dependent on the volume and concentration of the medication.

In the hospital, delivery of medication is often different. Delivery systems for inhaled medication vary. For patients with pulmonary disease, aerosol devices are attached to a respirator, the aerosolized medication is delivered into the respiratory system via a mouthpiece (mask, intubation devise, or nasal cannula) and inhalation is through the respirator. The respirator provides positive pressure to force the aerosol material into the lungs when the patient in intubated. However, if the patient is not intubated, the aerosolized medication is mixed with air inflow. The amount of medication is measured by the amount of liquid placed into the aerosol mechanism and delivered into the air stream, not the air volume. Thus, the only truly accurate current method of delivering respiratory medication is through intubation because of leakage of air and medication which occurs with other known devices.

Medical *Cannabis* has been approved in many states in the United States, and in a number of other countries, such as Canada. Recreational *Cannabis* has also been approved in some states and other countries.

*Cannabis*, also commonly known as marijuana, is a flowering plant that includes three species or sub-species, namely *sativa, indica* and *ruderalis*. The plant is indigenous to Central Asia and the Indian Subcontinent. *Cannabis* has long been used for hemp fiber, for oils, for medicinal purposes and as a recreational drug. *Cannabis* plants produce a group of chemicals called cannabinoids. The majority of these compounds are secreted by glandular trichomes that occur abundantly on the floral calyxes and bracts of female *Cannabis* plants. When used by humans medicinally or recreationally, *Cannabis* can be consumed by a variety of routes, including vaporizing or smoking dried flower buds and leaf portions, resins, extracted oils or waxes.

The most well-known cannabinoid is tetrahydrocannabinol, often abbreviated as "THC." The chemical formula for THC is $C_{21}H_{30}O_2$ and it has the following chemical structure:

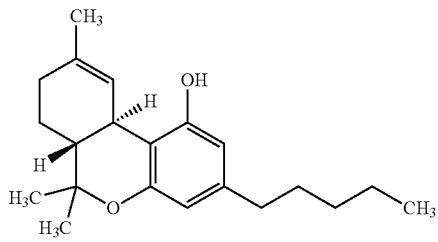 [SMILES: CCCCCc1cc(O)c2c(c1)OC(C)(C)[C@@H]1CCC(C)=C[C@@H]21]

THC is widely recognized as the principal psychoactive constituent in *Cannabis*. THC has a very low solubility in water, but good solubility in most organic solvents, specifically lipids and alcohols.

The *Cannabis* plant produces hundreds of other cannabinoids, terpenoids and other compounds that are only beginning to be identified, studied and categorized. One generally recognized cannabinoid that has medical efficacy is Cannabidiol ("CBD"). It is a major constituent of the plant, second to THC, and represents up to 40% by weight, in its extracts. Compared with THC, CBD is not psychoactive in healthy individuals, and may have a wider scope of medical applications than THC, including for epilepsy, multiple sclerosis spasms, anxiety disorders, bipolar disorder, schizophrenia, nausea, convulsion and inflammation, as well as inhibiting cancer cell growth.

It is also believed by many researchers that many of the other cannabinoids, terpenoids and other compounds in *Cannabis* may have important health benefits and/or be capable of treating certain human diseases.

In the early twentieth century, it became illegal in most of the world to cultivate or possess *Cannabis*. However, within the last decade, some states and nations have begun to legalize the cultivation, possession and use of *Cannabis* for medical purposes. Currently, the use of medical marijuana is decriminalized or legalized in many U.S. states. *Cannabis* is used to reduce nausea and vomiting during chemotherapy, to improve appetite in people with HIV/AIDS, to treat chronic pain, and help with muscle spasms. Other possible medical uses, which are sometimes disputed, include treatment of multiple sclerosis, AIDS wasting syndrome, epilepsy, rheumatoid arthritis, glaucoma, PTSD, depression and generalized anxiety.

Further, within the last five years, several states in the United States have legalized or decriminalized the cultivation, possession and use of *Cannabis* for recreational purposes. It is therefore estimated by many experts that *Cannabis* consumption, for both medical and recreational purposes, will increase over the coming years.

One now common way to consume *Cannabis*, for either medical or recreational purposes is via a vaporizer, sometimes called a "vape pen" or "electronic cigarette" or "e-cig." Other vaporization devices, such as balloon inhalers, also exist and are used for consumption of vaporized *Cannabis*. In general, vaporizers use heat to vaporize a mixture of extracted *Cannabis* oil or other *Cannabis* product and other carrier compounds, such as propylene glycol or vegetable glycerin.

As one article explained: "Vaporizers decarboxylate cannabinoid acids at about 200° C. and release neutral, volatile cannabinoids, which enter the systemic circulation via pulmonary absorption from the vapor. The non-pyrolytic vaporization avoids the formation of hazardous combustion products, such as tar, polycyclic aromatic hydrocarbons (PAH), carbon monoxide, and other carcinogens (e.g. benzene). Gieringer and co-workers demonstrated the advantages of *Cannabis* vaporization compared to smoking and showed that the formation of combustion products is suppressed almost completely." Published: Jan. 19, 2016 https://doi.org/10.1371/journal.pone.0147286.

Physicians are being asked to guide their patients in the use of both medical and recreational *Cannabis*. Many physicians are at a loss to help their patients. Physicians are trained to prescribe medication by dose and frequency. For example, "Take a 100 mg tablet, three times a day" is a typical way that medications are prescribed. In the case of the inhalers described above the patient is instructed to take two puffs, two or three times a day, depending upon their symptoms. However, due to the issues identified above with respect to inhalation devices and patient technique, the amount of medication delivered to any one patient is variable and there is no current method of accurately dosing inhaled marijuana vapor. Indeed, there is also no reliably accurate dosing available for most other inhaled medications, in view of the problems with the prior art pMDI's and holding chamber devices discussed herein.

Medical *Cannabis* does come in an oral preparation. Absorption is poor and variable.

Current oral preparations of THC, such as Marinol™ (Dronabinol), and of CBD, such as Epidiolex™, use synthetic versions of these compounds. Problems are occurring because the results do not fully emulate natural *Cannabis* and the complication rate with use is higher than with natural *Cannabis*.

According to https://b2b.gocaliva.com/the-rise-of-disposable-marijuana-vape-pens-in-califomia/ "*Cannabis* consumers across the state embrace the wands of *Cannabis* extract with such ardor that they command more market share than in any other state with legal recreational *Cannabis*. During the first quarter of 2018, vape sales captured 80 percent of the entire Golden State concentrates market according to *Cannabis* market research firm BDS Analytics."

A recent article stated "The pulmonary delivery of aerosolized THC-CBD solutions shows favorable pharmacokinetic properties, which are similar to those of an IV injection preparation. Adding a local anesthetic is recommended to prevent airways irritation and coughing, thus reducing the bioavailability. The negligible psychoactivity may result from the antipsychotic CBD, the low THC dosage, and/or the decreased formation of the psychoactive metabolite 11-OH-THC. Therefore, the inhalation via pMDI is an alternative to the oral administration route and an option for reliable and safe application of medical cannabinoids." *Med Cannabis Cannabinoids* 2018; 1:36-43 https://doi.org/10.1159/000489034

Inhaled Fentanyl works within 20.5 seconds, slightly faster than intravenous delivery of Fentanyl. It requires no IV and can be given immediately to an injured victim as long as they are breathing. Onset of the effect of intramuscular injections of Fentanyl take anywhere from five to thirty minutes after injection. Patients in shock will absorb medication slowly because of poor peripheral circulation due to shock which decreases peripheral blood flow. There is a need for having a loaded canister ready for immediate administration by simple inhalation, which would be a benefit to emergency medical teams and their patients.

Epidiolex is a new CBD medication for the treatment of certain seizure disorders. It is dosed twice a day by oral suspension. FIG. 3 (PRIOR ART) is a graph of blood concentrations of CBD over time with Epidiolex. In general, it takes four hours to get to maximum concentration. By twelve hours, plasma levels are almost zero and clearly out of therapeutic range.

Dronabinol is a synthetic THC medication, delivered in either oral solution or capsule. FIG. 4 (PRIOR ART) is a graph of blood concentrations of THC over time with the two different dosing forms of Dronabinol.

FIG. 5 (PRIOR ART) is a prior art graph of blood plasma mean concentration (mg/ml) of various cannabinoids over time, during smoking of a single *Cannabis* cigarette containing 3.55% of THC, with arrows indicating one inhalation or puff on the *Cannabis* cigarette.

FIG. 6 (PRIOR ART) is a prior art graph of mean concentration (ng/g) of CBD in the human brain, over time, after oral administration.

FIG. 7 (PRIOR ART) is a prior art graph of mean concentration (ng/g) of CBD in the human brain, over time, after administration by inhalation (vaping).

In general, after vaping the plasma concentration of THC (and also CBD) reaches maximum strength in 6 minutes and falls after 22 minutes. Adding vaped CBD to Epidiolex would allow a decrease in dosage of the oral medication and result in a more sustained plasma levels. This would reduce side effects, add natural CBD to the treatment, and add to efficacy. The key is to be able to accurately dose the vaped THC or CBD There are various pumps available to inflate toy balloons, such as the Qualatex Hand Held Air Inflator—Double Action Balloon Pump. The structure of these pumps, while not adequate to meet the quality requirements of a medical device, or to accomplish the objectives set forth herein, can be modified, adapted and improved as disclosed herein to achieve the goals and objectives of the positive pressure inhaler. These prior art devices have been used to construct prototypes and/or proof of concept devices by the Inventor. These balloon pumps generally have an intake system at one end of the pump and a plunging system that funnels the air from the chamber immediately adjacent to the intake portion of the pump. However, air flow is not well controlled. The pump configuration needs to be engineered to allow exact control of the inflow of air and medication into the chamber as well as the outflow of the medication mixture.

Accordingly, there is a need for an improved inhalation device for use with inhaled medications, including but not limited to medical *Cannabis*, which addresses the issues and disadvantages of prior art devices discussed above and that improves certainty of dosages and drug delivery to the lungs.

SUMMARY

Embodiments of the present invention address the needs described above and relate to a device and method of use for delivery of aerosolized medication to a patient, using positive pressure and a known volume of air and a known concentration of medication, in order to improve dosage certainty and drug delivery to the lungs. The disclosed embodiments address a device that implements a concept of adding a known amount of aerosolized or vaporized medication or other chemical to a known volume of air in a closed chamber. Said volume of air is then inhaled with positive pressure providing a known amount of medication to the patient's lungs.

The various embodiments of the present positive pressure inhaler has several features, no single one of which is solely responsible for its desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments solve the problems discussed in the Background and provide the advantages described herein.

In a first aspect, a positive pressure inhaler for delivery of inhalable medication to a patient is provided, which includes a pump chamber of known volume, including interior side walls, a piston that engages the interior side walls of the pump chamber, an inflow valve operably connected to the pump chamber, an outflow valve operably connected to the pump chamber, a patient delivery port operably connected to the outflow valve, wherein the piston is configured to have a piston travel length that is equal to or less than the length of the pump chamber, wherein the piston travel length defines a known delivery volume, where the pump chamber and piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation, where the pump chamber and piston are configured such that upon a second traversal of the piston through the pump chamber, the known volume of aerosolized/vaporized medication for patient inhalation will be displaced by the motion of the piston and expelled through the outflow valve and through the patient delivery port for positive pressure inhalation by the patient.

In an embodiment of the first aspect, the positive pressure inhaler also has a handle, where the handle is affixed to the piston and the handle is configured between the patient delivery port and the pump chamber.

In another embodiment of the first aspect, the positive pressure inhaler also has an inflow port for introduction of the aerosolized/vaporized medication into the positive pressure inhaler, where the inflow port is operably connected to the inflow valve.

In another embodiment of the first aspect, the inflow port is configured to accept insertion of a mouthpiece of a 510 thread vaporizer and wherein the inflow port is further configured to create a generally airtight seal between the inflow port and the mouthpiece upon insertion of the 510 thread vaporizer mouthpiece.

In another embodiment of the first aspect, the inflow port is configured to accept insertion of a mouthpiece of a positive metered dose inhaler ("pMDI") and where the inflow port is further configured to create a generally airtight seal between the inflow port and the mouthpiece upon insertion of the pMDI.

In another embodiment of the first aspect, the positive pressure inhaler also includes an inflow port valve that includes an inflow valve primary inflow port, an inflow valve discretionary inflow port, an inflow port valve outflow port, and an inflow port valve member, where the inflow valve outflow port is operably connected to the pump chamber inflow valve, where the inflow valve primary inflow port is operably connected to the inflow port, where the inflow port valve member is configured such that actuation of the inflow port valve member switches between a first position that enables flow from the inflow valve primary inflow port, and a second position that enables flow from the inflow valve discretionary inflow port, where the inflow port is configured to accept insertion of a medical device for generation of aerosolized/vaporized medication, where the inflow port is further configured to create a generally airtight seal between the inflow port and the outflow of the medical device for generation, whereby the inflow port valve member may be actuated to the first position to enable flow from the inflow valve primary inflow port so that a first defined volume of aerosolized/vaporized medication to be generated by the medical device for generation will be introduced into the pump chamber by negative pressure, and further whereby the inflow port valve member may be actuated to the second position to enable flow from the inflow valve discretionary inflow port.

In another embodiment of the first aspect, the inflow valve discretionary inflow port is operably connected to an opening to the atmosphere, so that a first defined volume of air may be introduced into the pump chamber by negative pressure to dilute the first defined volume of aerosolized/vaporized medication.

In another embodiment of the first aspect, the inflow valve discretionary inflow port is operably connected to a discretionary medical device, so that a second volume of a gas may be introduced into the pump chamber by negative pressure to dilute the first defined volume of aerosolized/vaporized medication.

In another embodiment of the first aspect, where the second volume of gas comprises a therapeutic gas.

In another embodiment of the first aspect, the therapeutic gas comprises pure oxygen.

In another embodiment of the first aspect, the second volume of gas is a second aerosolized/vaporized medication.

In another embodiment of the first aspect, the second aerosolized/vaporized medication is lidocaine.

In another embodiment of the first aspect, the medical device for generation is a pMDI and the inflow port is configured to accept insertion of the mouthpiece of the pMDI, and where the inflow port is further configured to create a generally airtight seal between the inflow port and the mouthpiece upon insertion of the pMDI.

In another embodiment of the first aspect, the medical device for generation is a 510 thread vaporizer and the inflow port is configured to accept insertion of the mouthpiece of the 510 thread vaporizer, and the inflow port is further configured to create a generally airtight seal between the inflow port and the mouthpiece upon insertion of the 510 thread vaporizer.

In another embodiment of the first aspect, the positive pressure inhaler also includes a 510 thread vaporizer rest, where the 510 thread vaporizer rest is configured to secure a battery section of the 510 thread vaporizer such that upon insertion of the mouthpiece of the 510 thread vaporizer into the inflow port and the insertion of the battery section into the 510 thread vaporizer rest, the weight of the battery section is supported to maintain the generally airtight seal between the inflow port and the mouthpiece.

In another embodiment of the first aspect, the inflow port valve is a ball valve.

In another embodiment of the first aspect, the positive pressure inhaler also includes a holding chamber that includes a chamber and an inflow port configured to accept insertion of a medical device for generation of aerosolized/vaporized medication, where the inflow port is further configured to create a generally airtight seal between the inflow port and an outflow port of the medical device for generation, and where the holding chamber is operably connected and in gas-tight communication with the inflow valve.

In another embodiment of the first aspect, the medical device for generation is a pMDI and the outflow port of the medical device for generation is a mouthpiece of the pMDI.

In another embodiment of the first aspect, the medical device for generation is a 510 thread vaporizer and the outflow port of the medical device for generation is a mouthpiece of the 510 thread vaporizer.

In another embodiment of the first aspect, the piston operably divides the pump chamber into a first section and a second section, wherein the inflow valve is operably connected to the first section of the pump chamber, where the outflow valve is operably connected to the first section of the pump chamber, and the positive pressure inhaler also includes a secondary inflow valve operably connected to a second section of the pump chamber, a secondary outflow valve operably connected to the second section of the pump chamber and the patient delivery port, and where the pump chamber, the piston, the inflow valve, the outflow valve, the secondary inflow valve and the secondary outflow valve are configured such that the positive pressure inhaler has a double-action such that upon the second traversal of the piston through the pump chamber and while the aerosolized/vaporized medication is displaced from the first section of the pump chamber and through the patient delivery port, a second dose of aerosolized/vaporized medication will be drawn through the secondary inflow valve into the second section of the pump chamber.

In another embodiment of the first aspect, upon a third traversal of the piston through the pump chamber, and while the second dose of aerosolized/vaporized medication is displaced from the second section of the pump chamber and through the patient delivery port, a third dose of aerosolized/vaporized medication will be drawn through the inflow valve into the first section of the pump chamber.

In another embodiment of the first aspect, the positive pressure inhaler also has a transparent viewing pane that enables viewing of the pump chamber to verify that it contains aerosolized/vaporized medication.

In another embodiment of the first aspect, the positive pressure inhaler also has a motor operably connected to the piston, where the motor is configured to drive the first traversal of the piston.

In another embodiment of the first aspect, the positive pressure inhaler also has a flow rate indicator.

In another embodiment of the first aspect, the flow rate indicator indicates the rate of travel of the piston.

In another embodiment of the first aspect, the positive pressure inhaler also has a volume indicator, where the volume indicator indicates the distance that the piston has travelled during the first traversal the piston.

In another embodiment of the first aspect, the positive pressure inhaler also has an adjustable stop to control the amount of aerosolized/vaporized medication drawn into pump chamber.

In another embodiment of the first aspect, the positive pressure inhaler also has a notification device to notify a user when a defined portion of the pump chamber has been filled with aerosolized/vaporized medication.

In another embodiment of the first aspect, the notification device emits a sound.

In another embodiment of the first aspect, the notification device emits a light.

In another embodiment of the first aspect, the patient delivery port comprises a patient mouthpiece.

In another embodiment of the first aspect, patient mouthpiece is removable.

In another embodiment of the first aspect, the positive pressure inhaler also has a one-way anti-blowback valve to prevent the patient from pushing aerosolized/vaporized medication back through the patient delivery port and into the pump chamber.

In a second aspect, a method of delivering a known volume of aerosolized/vaporized medication to the lungs of a patient under positive pressure is provided, the method including selecting a positive pressure inhaler that includes a pump chamber of known volume, including interior side walls, a piston that engages the interior side walls of the pump chamber, an inflow valve operably connected to the pump chamber, an outflow valve operably connected to the pump chamber, a patient delivery port operably connected to the outflow valve, where the piston is configured to have a piston travel length that is equal to or less than the length of the pump chamber, where the piston travel length defines a known delivery volume, wherein the pump chamber and piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation, where the pump chamber and piston are configured such that upon a second traversal of the piston through the pump chamber, the known volume of aerosolized/vaporized medication for patient inhalation will be displaced by the motion of the piston and expelled through the outflow valve and through the patient delivery port for positive pressure inhalation by the patient, affixing a medical device to the input port, traversing the piston a first time through the pump chamber and generating negative pressure, thereby drawing aerosolized/vaporized medication into the pump chamber through the inflow valve, creating a known volume of aerosolized/vaporized medication for patient inhalation, closing the patient's lips over the patient delivery port, traversing the piston a second time through the pump chamber thereby displacing the known volume of aerosolized/vaporized medication by the motion of the piston and expelling the known volume of aerosolized/vaporized medication through the outflow valve and through the patient delivery port, and causing the patient to inhale the known volume of aerosolized/vaporized medication under positive pressure.

In an embodiment of the second aspect, the positive pressure inhaler further comprises a handle, wherein the handle is affixed to the piston and the handle is configured between the patient delivery port and the pump chamber.

In another embodiment of the second aspect, the positive pressure inhaler also has an inflow port for introduction of the aerosolized/vaporized medication into the positive pressure inhaler, where the inflow port is operably connected to the inflow valve.

In another embodiment of the second aspect, the inflow port is configured to accept insertion of a mouthpiece of a 510 thread vaporizer and the inflow port is further configured to create a generally airtight seal between the inflow port and the mouthpiece upon insertion of the 510 thread vaporizer mouthpiece.

In another embodiment of the second aspect, the inflow port is configured to accept insertion of a mouthpiece of a positive metered dose inhaler ("pMDI") and the inflow port is further configured to create a generally airtight seal between the inflow port and the mouthpiece upon insertion of the pMDI.

In another embodiment of the second aspect, the positive pressure inhaler also has an inflow port valve including an inflow valve primary inflow port, an inflow valve discretionary inflow port, an inflow port valve outflow port, and an inflow port valve member, where the inflow valve outflow port is operably connected to the pump chamber inflow valve, where the inflow valve primary inflow port is operably connected to the inflow port, where the inflow port valve member is configured such that actuation of the inflow port valve member switches between a first position that enables flow from the inflow valve primary inflow port, and a second position that enables flow from the inflow valve discretionary inflow port, where the inflow port is configured to accept insertion of a medical device for generation of aerosolized/vaporized medication, where the inflow port is further configured to create a generally airtight seal between the inflow port and the outflow of the medical device for generation, whereby the inflow port valve member may be actuated to the first position to enable flow from the inflow valve primary inflow port so that a first defined volume of aerosolized/vaporized medication to be generated by the medical device for generation will be introduced into the pump chamber by negative pressure, and further whereby the inflow port valve member may be actuated to the second position to enable flow from the inflow valve discretionary inflow port, and the method also includes actuating the inflow port valve member to select between the inflow valve primary inflow port and the inflow valve discretionary inflow port.

In another embodiment of the second aspect, the inflow valve discretionary inflow port is operably connected to an opening to the atmosphere, so that a first defined volume of air is be introduced into the pump chamber by negative pressure to dilute the first defined volume of aerosolized/vaporized medication.

In another embodiment of the second aspect, the inflow valve discretionary inflow port is operably connected to a discretionary medical device, so that a second volume of a gas may be introduced into the pump chamber by negative pressure to dilute the first defined volume of aerosolized/vaporized medication.

In another embodiment of the second aspect, the second volume of gas comprises a therapeutic gas.

In another embodiment of the second aspect, the therapeutic gas comprises pure oxygen.

In another embodiment of the second aspect, the second volume of gas is a second aerosolized/vaporized medication.

In another embodiment of the second aspect, the second aerosolized/vaporized medication is lidocaine.

In another embodiment of the second aspect, the medical device for generation is a pMDI and the inflow port is configured to accept insertion of the mouthpiece of the pMDI and the inflow port is further configured to create a generally airtight seal between the inflow port and the mouthpiece upon insertion of the pMDI.

In another embodiment of the second aspect, the medical device for generation is a 510 thread vaporizer and the inflow port is configured to accept insertion of the mouthpiece of the 510 thread vaporizer and the inflow port is further configured to create a generally airtight seal between the inflow port and the mouthpiece upon insertion of the 510 thread vaporizer.

In another embodiment of the second aspect, the positive pressure inhaler also has a 510 thread vaporizer rest, where the 510 thread vaporizer rest is configured to secure a battery section of the 510 thread vaporizer such that upon insertion of the mouthpiece of the 510 thread vaporizer into the inflow port and the insertion of the battery section into the 510 thread vaporizer rest, the weight of the battery section is supported to maintain the generally airtight seal between the inflow port and the mouthpiece.

In another embodiment of the second aspect, the inflow port valve is a ball valve.

In another embodiment of the second aspect, the positive pressure inhaler also has a holding chamber comprising a chamber and an inflow port configured to accept insertion of a medical device for generation of aerosolized/vaporized medication, where the inflow port is further configured to create a generally airtight seal between the inflow port and an outflow port of the medical device for generation, and wherein the holding chamber is operably connected to the inflow valve.

In another embodiment of the second aspect, the medical device for generation is a pMDI and the outflow port of the medical device for generation is a mouthpiece of the pMDI.

In another embodiment of the second aspect, the medical device for generation is a 510 thread vaporizer and the outflow port of the medical device for generation is a mouthpiece of the 510 thread vaporizer.

In another embodiment of the second aspect, the piston operably divides the pump chamber into a first section and a second section, where the inflow valve is operably connected to the first section of the pump chamber, where the outflow valve is operably connected to the first section of the pump chamber, and has a secondary inflow valve operably connected to a second section of the pump chamber, a secondary outflow valve operably connected to the second section of the pump chamber and the patient delivery port, where the pump chamber, the piston, the inflow valve, the outflow valve, the secondary inflow valve and the secondary outflow valve are configured such that the positive pressure inhaler has a double-action such that upon the second traversal of the piston through the pump chamber and while the aerosolized/vaporized medication is displaced from the first section of the pump chamber and through the patient delivery port, a second dose of aerosolized/vaporized medication will be drawn through the secondary inflow valve into the second section of the pump chamber.

In another embodiment of the second aspect, upon a third traversal of the piston through the pump chamber, and while the second dose of aerosolized/vaporized medication is displaced from the second section of the pump chamber and through the patient delivery port, a third dose of aerosolized/vaporized medication will be drawn through the inflow valve into the first section of the pump chamber.

In a third aspect, a method of delivering medication to a patient via patient respiration is provided including selecting a pump chamber with a known volume, dispersing a first aerosolized/vaporized medication in the known volume of the pump chamber, sealing the pump chamber thereby preventing additional air from entering the known volume of the pump chamber and diluting the first aerosolized/vaporized medication in the known volume of the pump chamber, operably engaging a patient's air passage with a patient delivery port that is operably connected to the pump chamber, and using positive pressure to displace the first aerosolized/vaporized medication from the known volume of the pump chamber and through the patient delivery port so as to deliver the first aerosolized/vaporized medication to the patient's air passage and into the patient's lungs with positive pressure while the patient draws a breath.

In an embodiment of the third aspect, the patient draws multiple breaths to complete the step of delivering the first aerosolized/vaporized medication to the patient's air passage and into the patient's lungs.

In another embodiment of the third aspect, the patient delivery port is a mouthpiece and the operably engaging step includes causing the patient to close the patient's lips over the mouthpiece.

In another embodiment of the third aspect, the patient delivery port is a nasal cannula with two prongs, and the operably engaging step includes causing the patient to insert the prongs into the patient's nostrils.

In another embodiment of the third aspect, the patient delivery port is a mask, and the operably engaging step includes covering the patient's nose and mouth with the mask.

In another embodiment of the third aspect, after delivering the first aerosolized/vaporized medication to the patient's air passage, and before the patient exhales, delivering supplemental air to the patient's air passage under positive pressure to force the first aerosolized/vaporized medication deeper into the patient's lungs.

In another embodiment of the third aspect, the first aerosolized/vaporized medication comprises at least two medications in a mixture.

In another embodiment of the third aspect, after patient exhalation of the first aerosolized/vaporized medication, dispersing a second aerosolized/vaporized medication in the known volume of the pump chamber, sealing the pump chamber thereby preventing additional air from entering the known volume of the pump chamber and diluting the second aerosolized/vaporized medication in the known volume of the pump chamber, using positive pressure to displace the second aerosolized/vaporized medication from the known volume of the pump chamber and through the patient delivery port so as to deliver the second aerosolized/vaporized medication to the patient's air passage and into the patient's lungs with positive pressure while the patient draws a breath.

In another embodiment of the third aspect, the second aerosolized/vaporized medication is different than the first aerosolized/vaporized medication.

In another embodiment of the third aspect, the first aerosolized/vaporized medication is a numbing agent and the second aerosolized/vaporized medication is a pulmonary medication.

In another embodiment of the third aspect, the first aerosolized/vaporized medication is lidocaine and the second aerosolized/vaporized medication is albuterol.

In a fourth aspect, an aerosol/vaporizer medication dosage testing system is provided, including a plurality of positive pressure inhalers, each of which has a pump chamber of known volume, including interior side walls, a piston that engages the interior side walls of the pump chamber, an inflow valve operably connected to the pump chamber, an outflow valve operably connected to the pump chamber, a patient delivery port operably connected to the outflow valve, where the piston is configured to have a piston travel length that is equal to or less than the length of the pump chamber, where the piston travel length defines a known delivery volume, where the pump chamber and piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation, where the pump chamber and piston are configured such that upon a second traversal of the piston through the pump chamber, the known volume of aerosolized/vaporized medication for patient inhalation will be displaced by the motion of the piston and expelled through the outflow valve and through the patient delivery port for positive pressure inhalation by the patient, and a volumetric testbed including a support table on which the plurality of positive pressure inhalers are mounted, a receiver valve, where the receiver valve is in airtight communication with each of the patient delivery ports of each of the plurality of positive pressure inhalers, and a capture vessel, where the receiver valve is in airtight communication with the capture vessel, configured such that, upon traversal of each of the respective pistons of each of the plurality of positive pressure inhalers, the respective aerosolized/vaporized medication of each of the positive pressure inhalers is displaced through the receiver valve and into the capture vessel.

In an embodiment of the fourth aspect, the receiver valve is configured as a one-way valve biased toward the capture vessel.

In another embodiment of the fourth aspect, the capture vessel comprises an inflatable balloon.

In another embodiment of the fourth aspect, the capture vessel comprises a closure valve, such that when closed, the closure valve prevents escape of the respective aerosolized/vaporized medication of each of the positive pressure inhalers and further enables removal of the capture vessel from airtight communication with the receiver valve.

In a fifth aspect, a method of testing aerosol/vaporizer medication dosages is provided, the method including providing an aerosol/vaporizer medication dosage testing system that includes a plurality of positive pressure inhalers, each of which has a pump chamber of known volume, including interior side walls, a piston that engages the interior side walls of the pump chamber, an inflow valve operably connected to the pump chamber, an outflow valve operably connected to the pump chamber, a patient delivery port operably connected to the outflow valve, where the piston is configured to have a piston travel length that is equal to or less than the length of the pump chamber, wherein the piston travel length defines a known delivery volume, where the pump chamber and piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation, where the pump chamber and piston are configured such that upon a second traversal of the piston through the pump chamber, the known volume of aerosolized/vaporized medication for patient inhalation will be displaced by the motion of the piston and expelled through the outflow valve and through the patient delivery port for positive pressure inhalation by the patient, and a volumetric testbed including a support table on which the plurality of positive pressure inhalers are mounted, a receiver valve, where the receiver valve is in airtight communication with each of the patient delivery ports of each of the plurality of positive pressure inhalers, and a capture vessel, where the receiver valve is in airtight communication with the capture vessel, configured such that, upon traversal of each of the respective pistons of each of the plurality of positive pressure inhalers, the respective aerosolized/vaporized medication of each of the positive pressure inhalers is displaced through the receiver valve and into the capture vessel, connecting a plurality of identical medical devices equipped with the same medication to the respective plurality of inflow ports of the plurality of positive pressure inhalers, traversing the piston of each of the respective positive pressure inhalers to provide a first draw sample aerosolized/vaporized medication from each of the respective positive pressure inhalers and collecting it in the capture vessel, and removing the capture vessel and analyzing the concentration of aerosolized/vaporized medication per unit volume based on the known volume of the plurality of positive pressure inhalers and the number of the plurality of positive pressure inhalers.

BRIEF DESCRIPTION OF THE DRAWINGS

In the descriptions that follow, like parts or steps are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 11 are schematic illustrations of a delivery chamber cap for the positive pressure inhaler, for connection to an aerosol medication device such as a vape pen, a pMDI or another vaporizer.

DETAILED DESCRIPTION OF THE EMBODIMENTS

Figure 1:
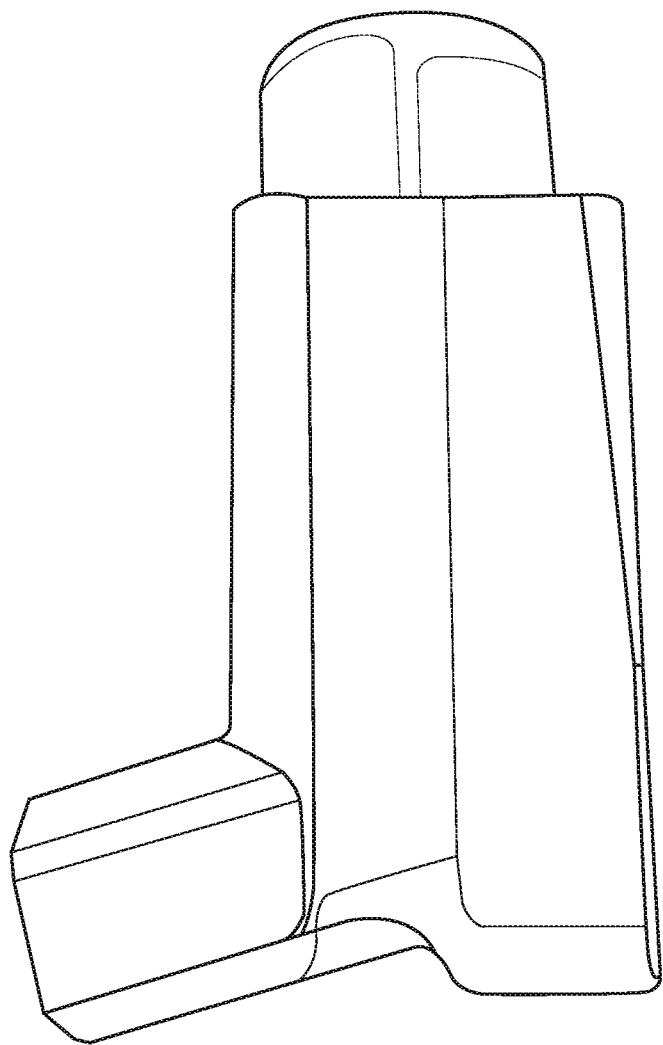
FIG. 1 (PRIOR ART) illustrates a prior art pressurized Metered Dose Inhaler ("pMDI")
Figure 2:
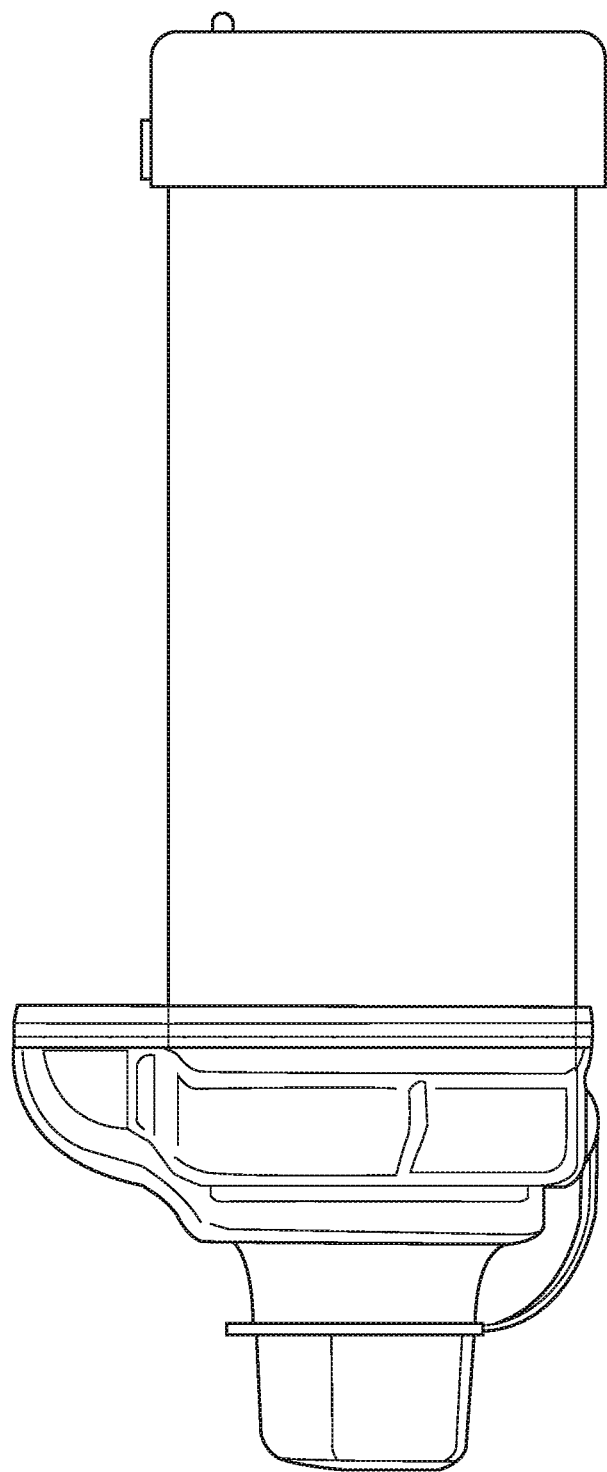
FIG. 2 (PRIOR ART) illustrates a prior art respiratory holding chamber, for use with a pMDI.
Figure 3:
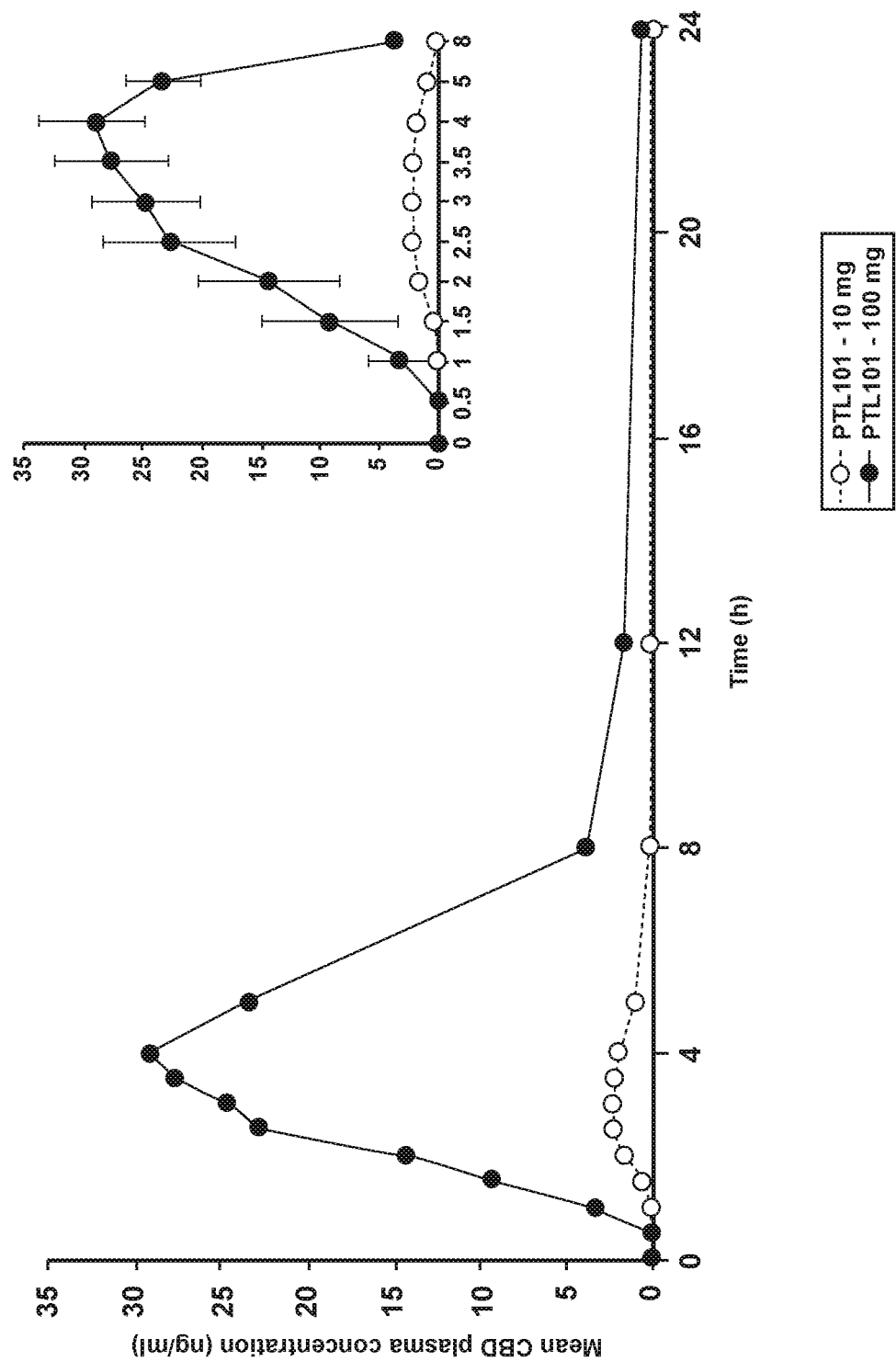
FIG. 3 (PRIOR ART) is a prior art graph of blood concentrations of CBD over time with a twice-daily orally-administered solution of Epidiolex.
Figure 4A:
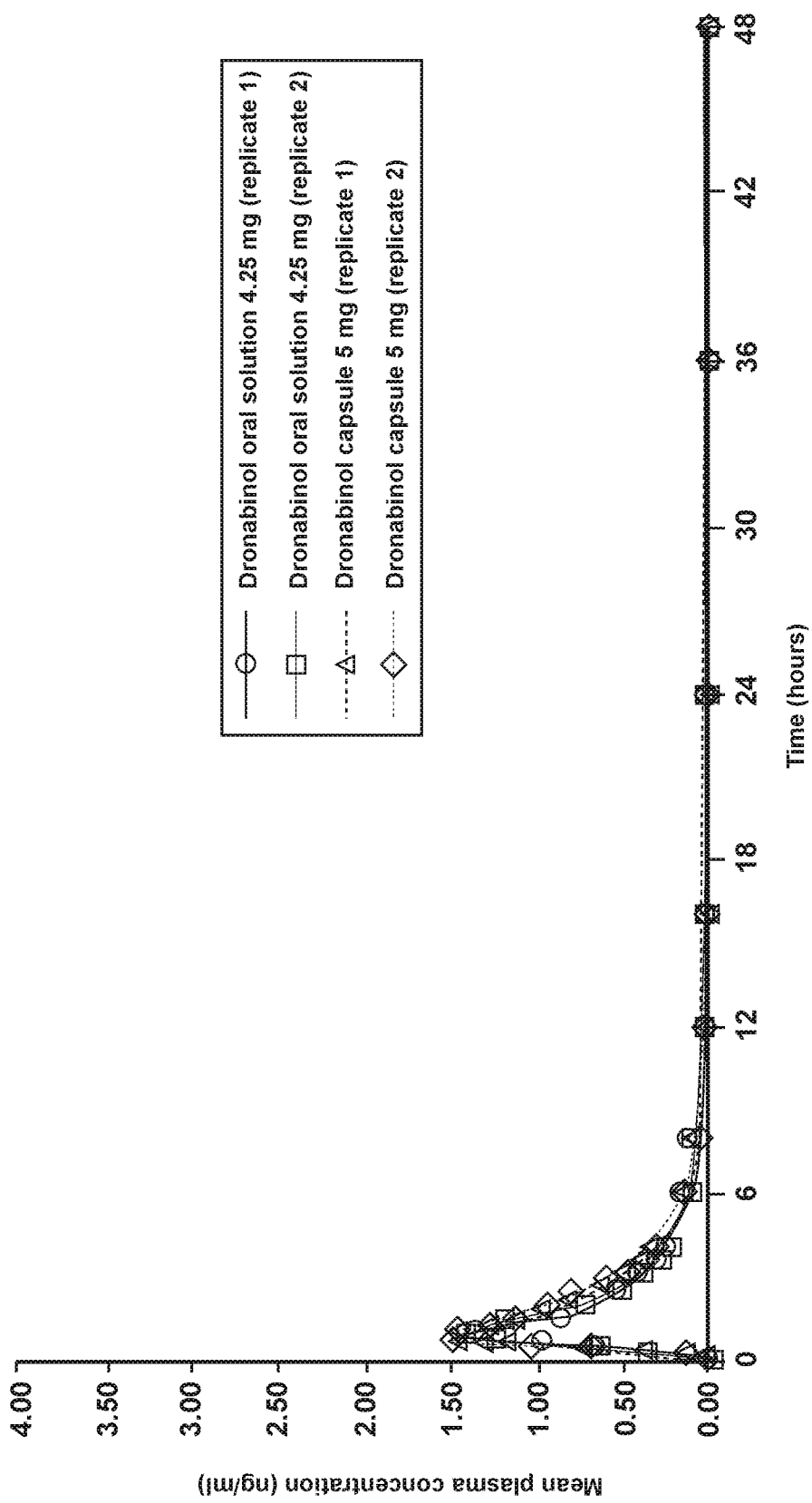
FIGS. 4A (PRIOR ART) and 4B (PRIOR ART) are prior art graphs of blood plasma mean concentration (mg/ml) of THC over time, from administration of two forms of Dronabinol, including an oral solution of 4.25 mg and a capsule of 5 mg.
Figure 4B:
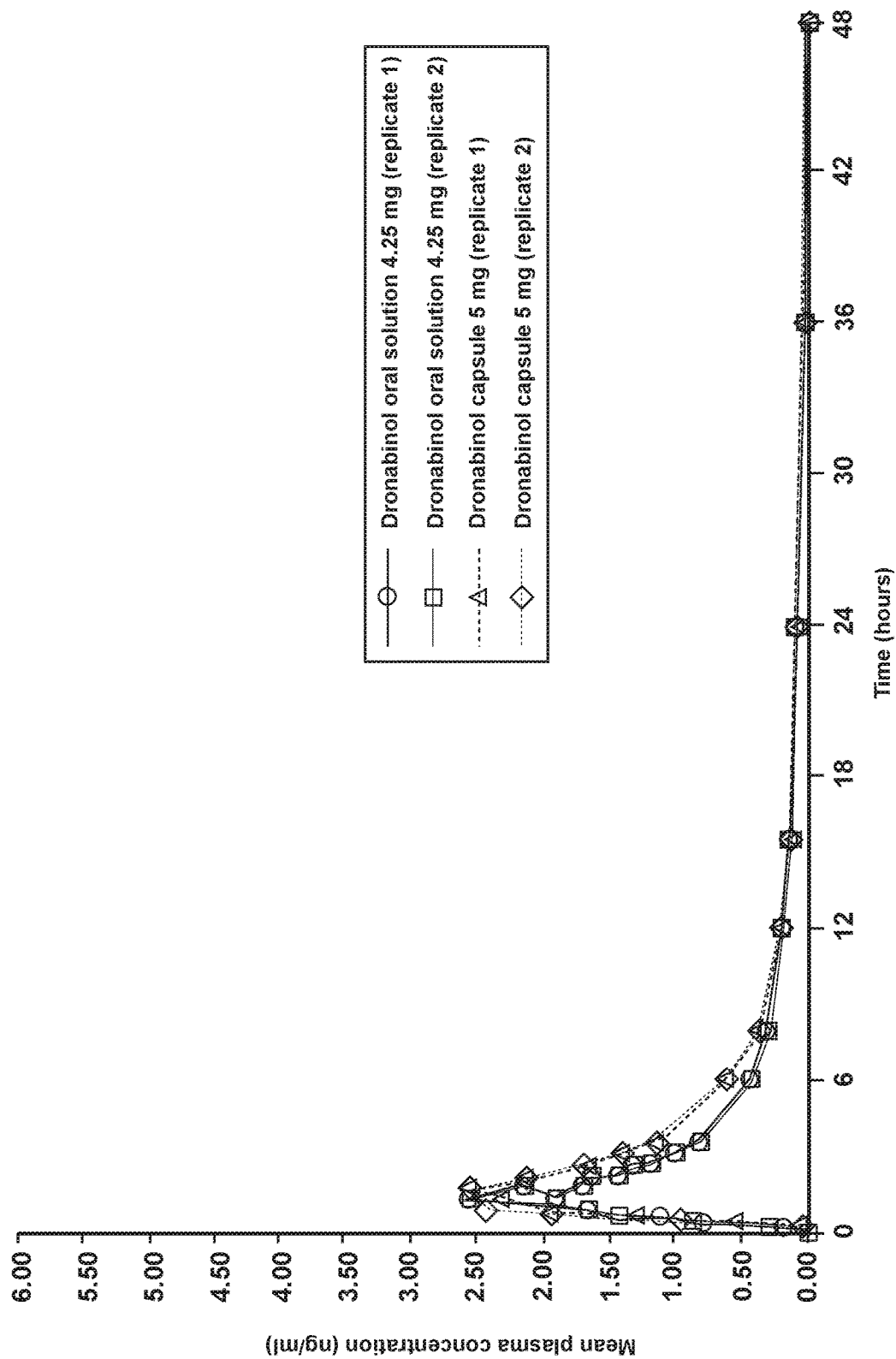
Figure 5:
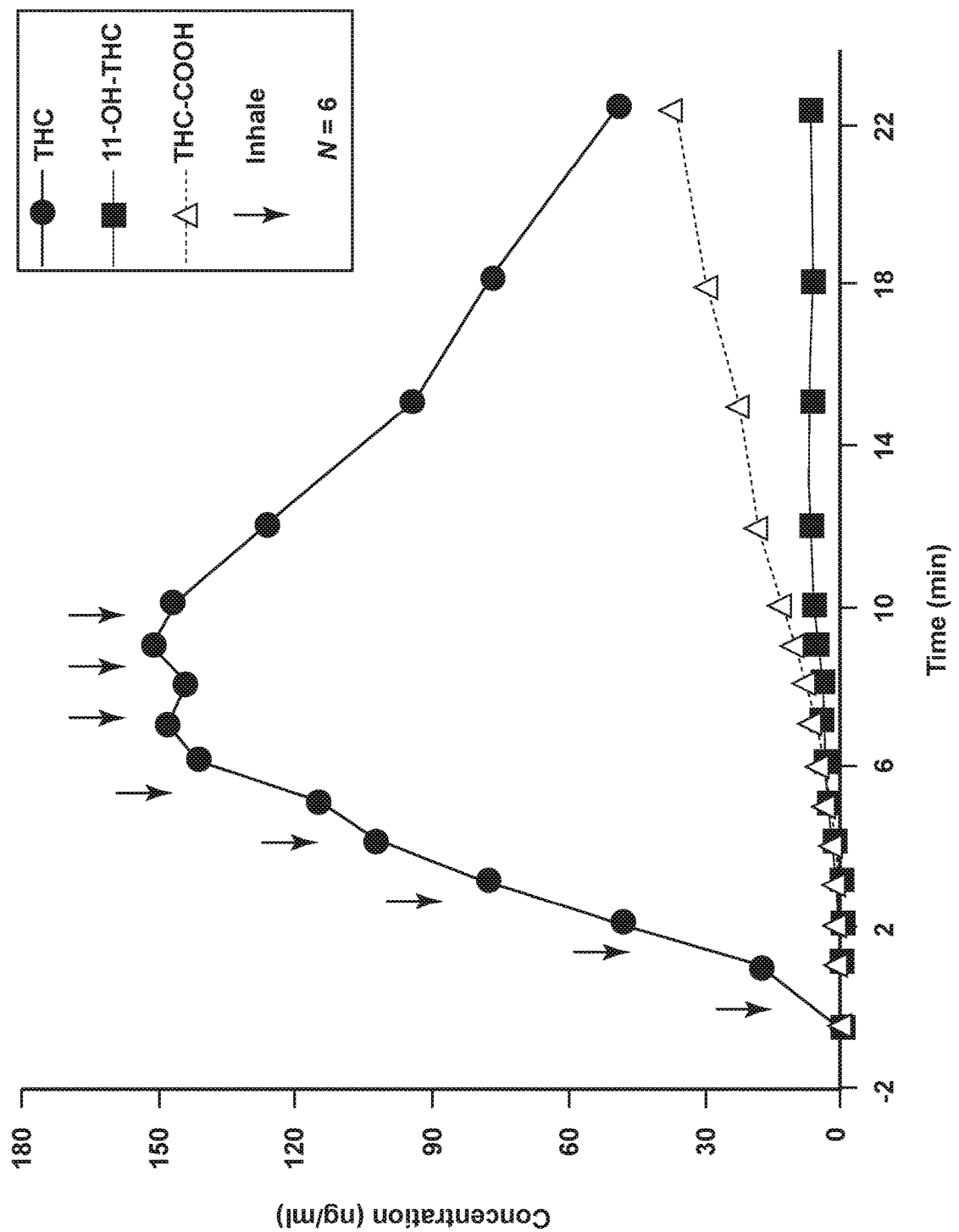
FIG. 5 (PRIOR ART) is a prior art graph of blood plasma mean concentration (mg/ml) of various cannabinoids over time, during smoking of a single *Cannabis* cigarette containing 3.55% of THC, with arrows indicating one inhalation or puff on the *Cannabis* cigarette.
Figures 6, 7:
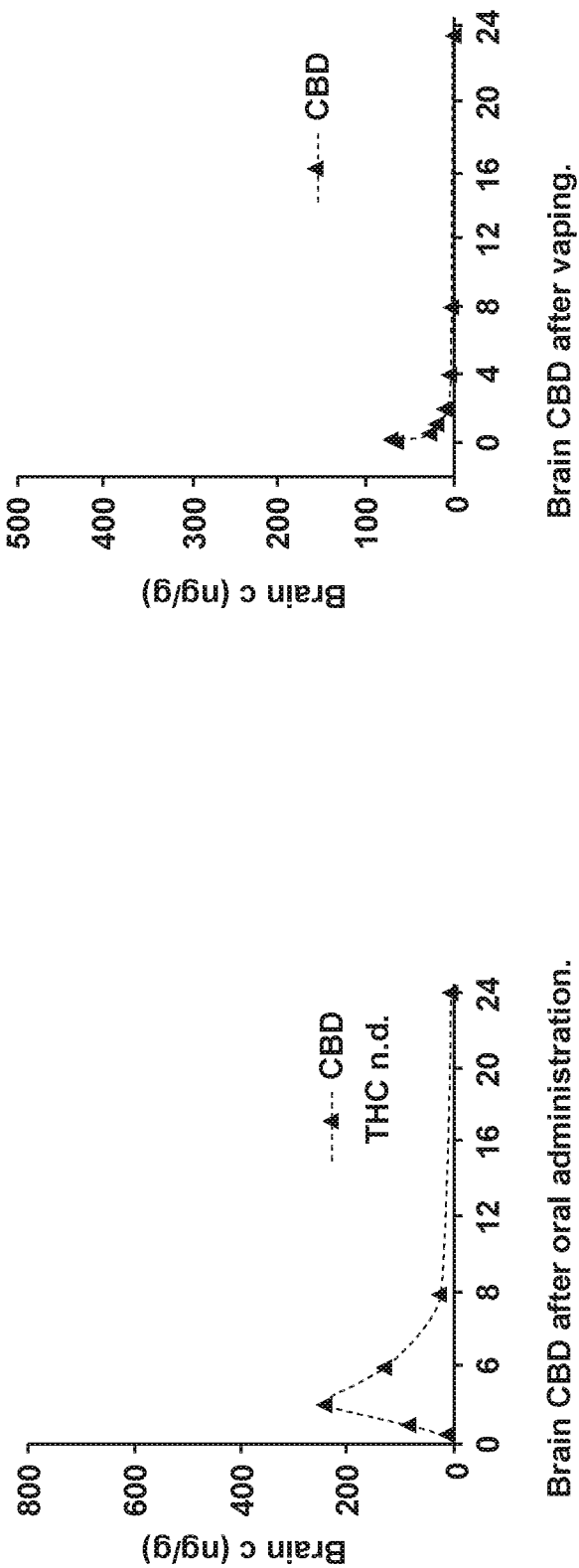
FIG. 6 (PRIOR ART) is a prior art graph of mean concentration (ng/g) of CBD in the human brain, over time, after oral administration.
FIG. 7 (PRIOR ART) is a prior art graph of mean concentration (ng/g) of CBD in the human brain, over time, after administration by inhalation (vaping)
Figure 8:
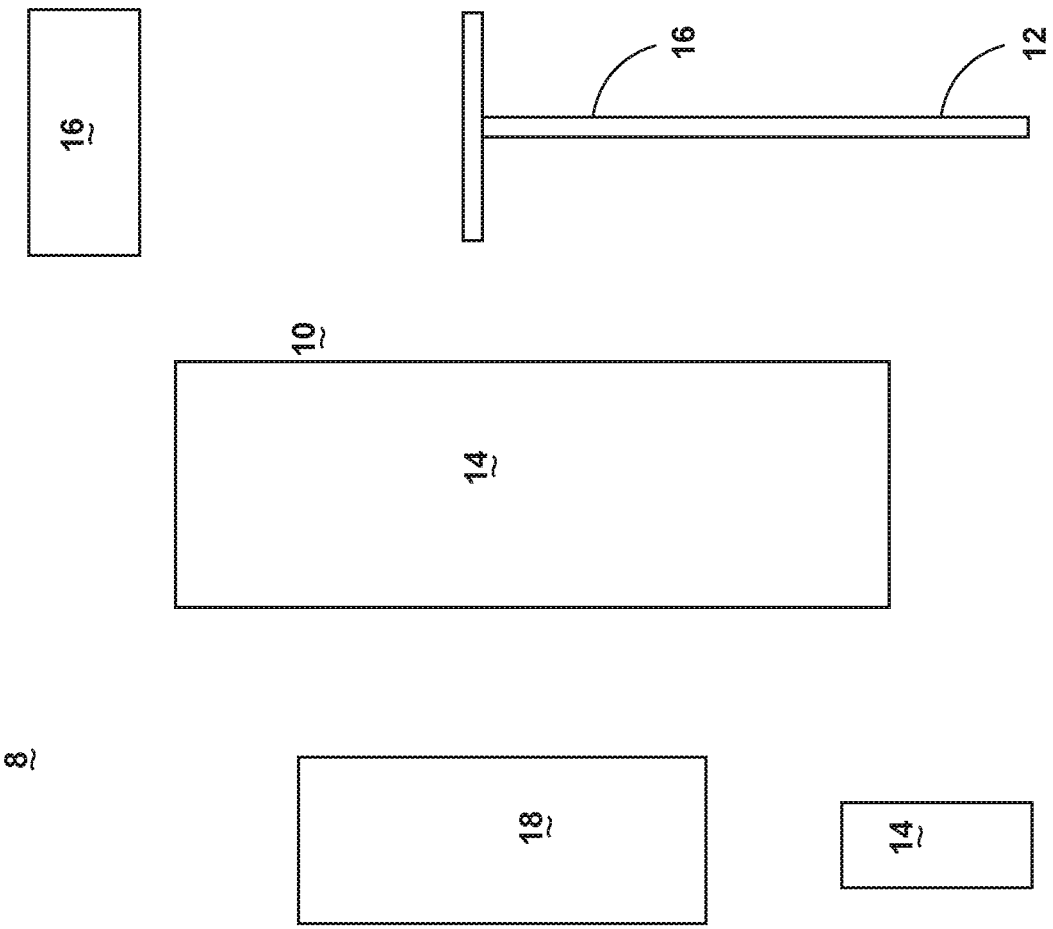
FIG. 8 is a schematic illustration of elements of a first embodiment a positive pressure inhaler.
Figure 9:
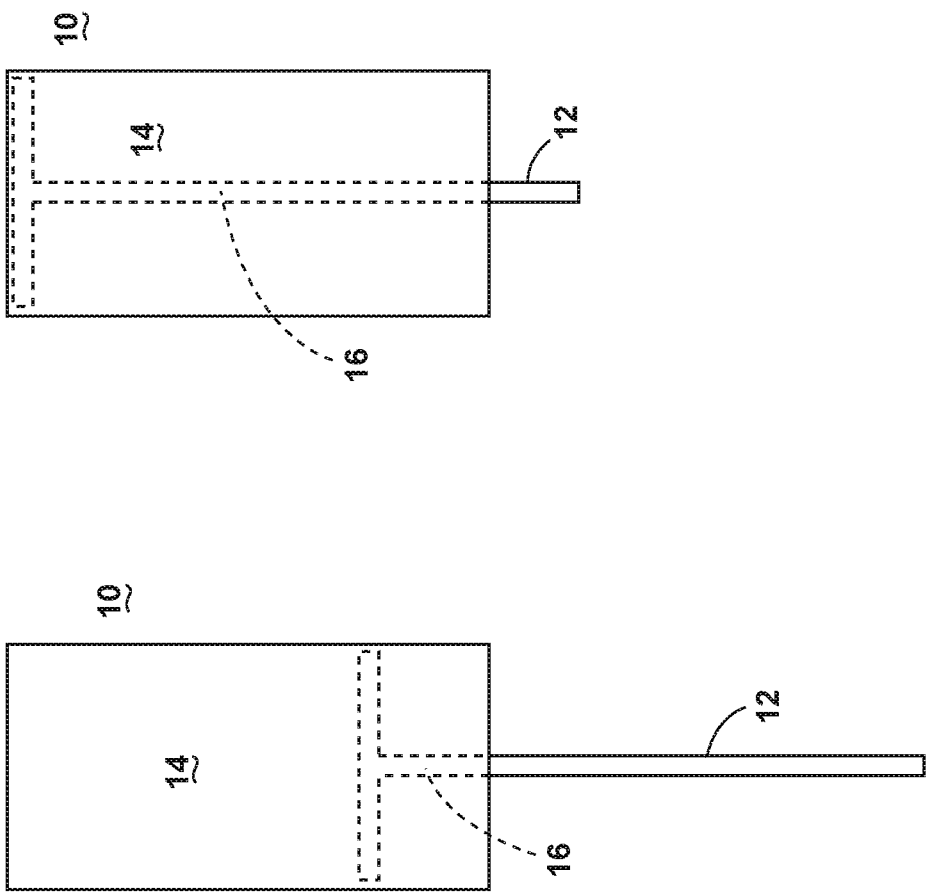
FIG. 9 is a schematic illustration of the interaction of certain elements of the first embodiment of the positive pressure inhaler.
Figure 10:
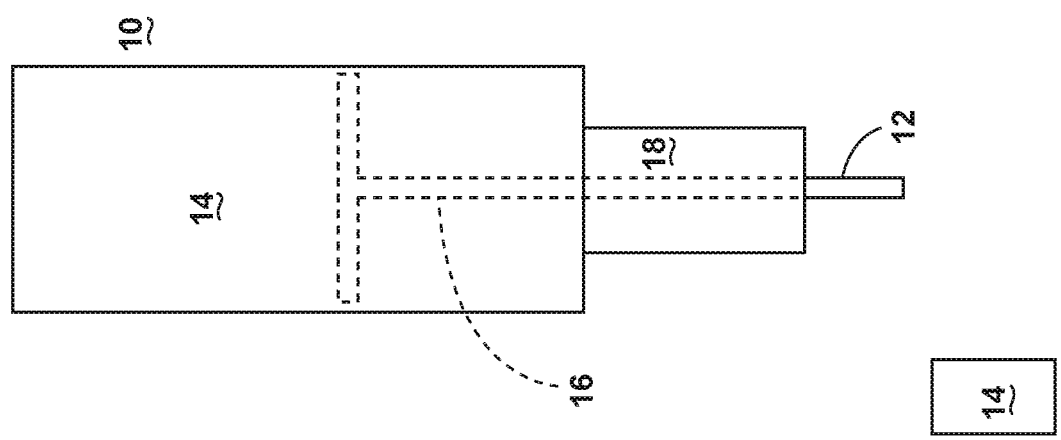
FIG. 10 is a further schematic illustration of the interaction of certain elements of the first embodiment of the positive pressure inhaler.

The description that follows is presented to enable one skilled in the art to make and use the present invention, and is provided in the context of a particular application and its requirements. Various modifications to the disclosed embodiments will be apparent to those skilled in the art, and the general principles discussed may be applied to other embodiments and applications without departing from the scope and spirit of the invention. Therefore, the invention is not intended to be limited to the embodiments disclosed, but the invention is to be given the largest possible scope which is consistent with the principles and features described herein.

Embodiments disclosed herein relate to a device for a hand operated pump, or chamber configured as a pump, for the purposes of delivering medication, aerosol, vaporized smoke or fumigant to a patient's lungs and possibly providing positive pressure during the administration of said medication or vapor. Embodiments disclosed herein further disclose and address a method for adding a known amount of medication, to a known volume of air or gas, to provide accurate administration of inhaled medication, using any suitable delivery system that achieves these requirements.

Embodiments of the invention, referred to generally herein as a positive pressure inhaler, include a closed chamber into which medication, aerosol, vaporized smoke or fumigant can be added. The patient then sucks (inhales) from the closed chamber while using the pump to exert positive pressure on the closed chamber, thereby causing the volume of the chamber to decrease and the medication to be delivered into lungs and oropharynx via both the patient inhalation and the positive pressure. This is in contrast to current respiratory chambers and pMDI's that are open and allow air to mix with the medication during the inhalation, and which do not rely upon positive pressure from a closed volume of air to drive the medication into the patient's lungs.

Embodiments of the disclosed positive pressure inhaler device relies on positive pressure to deliver an accurate dose of medication into the lung. The device relies on the known volume of a delivery chamber, into which a known volume of aerosolized or vaporized medication is introduced, to determine the dosage delivered to the patient or user. This device can be used for aerosols, any kind of warm or cool vapor, and any other material that can be delivered in a gaseous state or suspended in air. This includes *Cannabis* products, nicotine products, narcotic medication, and any aerosolized medication.

All of these compounds can be delivered by this device, allowing accurate dosage of the compounds. Small amounts of an inhaled drug can augment oral administration of the drug. This delivery system allows for an accurate delivery of such medication. By combining inhaled and oral medication the systemic concentration can be even, and, potentially, the oral dosage of medication reduced.

Furthermore, since the delivery chamber measures the volume of the inhaled material, dosage can be controlled. Doses can be measured and altered to meet the patient's (consumer's) needs. The doses and concentrations can be changed by varying the volume of air in the chamber and the amount of outside air that is allowed to blend with the aerosol and the dosage of medication delivered into the chamber. Altering the ratio of medication to air controls the dose and ease of use. This allows for lower or higher concentrations of medication (without changing the dose of the medication). Patients who cannot tolerate high concentrations of inhaled medication can be provided with lower concentrations of medication without changing the dose of the medication by changing the volume of the chamber. Inflow of medication or Marijuana vapor into the chamber can be controlled, thus controlling the concentration of medicine in the chamber.

The system also allows the patient to deliver to himself positive pressure at a rate comfortable to the patient during the delivery of medication. This may overcome some upper respiratory resistance. The patient can push the medication down into the alveoli where absorption is better. Positive pressure improves absorption.

The patient can deliver the medication and use as many breaths as is required since the amount of medication drawn into the chamber is controlled and reproducible. Whether the user uses one inhalation breath, two inhalation breaths, or as many as five to seven inhalation breaths, to empty the delivery chamber, this will not affect the ultimate medication dosage. The volume going into the lungs determines the amount of medication delivered. One or more breaths can be used without changing the concentration of the medication. Aerosolized medication cannot escape from the generally sealed delivery chamber (except as intended through the piston end/mouthpiece for delivery to the patient's lungs) and the amount of medication delivered is constant and reproducible. The amount of medication delivered is determined by the volume that is inhaled. Coughing or stopping only affects the amount of medication that was inhaled in that one breath. In some embodiments, the delivery chamber and/or piston may include a "double-action" that allows a volume of air to be added to the inhalation after the medication has been delivered by the first stroke of the piston. On a second piston stroke of the double action system, the air (now without additional medication) will further serve to force medication inhaled during the first piston stroke further into the patient's lungs.

The dose of the medication is not dependent on how big a breath the patient can take. If during inhalation the patient coughs, this does not destroy the entire delivered amount of medication but only the medication that is in the lungs during that particular inhalation breath. Chronic obstructive pulmonary disease which may limit the amount of air taken in at any one time will not affect overall dose of the medication since as many breadths as needed can be used to empty the chamber.

In the study (*Marijuana Smoking: Effects of Varying Puff Volume and Breathholding*) subjects were taught to inhale 30, 60, or 90 ml. By teaching them to inhale a known volume, they were able to quantify the volume inhaled and the dose of medication. The researchers of that study suggested a local inhaled anesthetic to prevent coughing. However, they failed to recognize that by diluting the concentration of medication they could ease the irritation to the respiratory tract. The embodiments of the positive pressure inhaler device disclosed herein, allow the dose of medication to be diluted, by volume, to maintain the same dosage at a lower concentration, thus avoiding irritation to the respiratory tract. Furthermore, the patient using the disclosed positive pressure inhaler device can take multiple breaths to achieve the same medication dosage. Research cannot be conducted on a medication if the dosage cannot be controlled and measured. The presently disclosed positive pressure inhaler device allows the actual dosage of medication inhaled to be controlled and quantified.

Embodiments of the disclosed positive pressure inhaler device also allow for the addition of supplemental oxygen or the delivery of a combination of two or more medications at the same time, by combining two or more medications into the delivery chamber at the same time, if the mediations are compatible. Further, the disclosed embodiments allow the patient to deliver the medication as slow or as fast as the patient can tolerate. The patient can even stop and rest for a few breaths before continuing to deliver the rest of the medication.

Current users of medical marijuana have no way of accurately controlling the dose of medication they receive. Every time they change to a new product, such as buying a new cartridge for their vape pen, they have to experiment until they find the right dosage. By quantifying the dosage delivery system, embodiments of the disclosed positive pressure inhaler allow the patient to deliver medication accurately. *Cannabis* oil for vaporization is usually produced in batches. Typically, a manufacturer will produce large volumes of liquid that is then placed into small cartridges. Hundreds or thousands of cartridges are produced. By using a known vaporization device such as a vape pen, in combination with a positive pressure inhaler, also referred to herein as a "volume inhaler," the dosage of each administration of *Cannabis* may be accurately measured. The manufacturer can use an embodiment of the positive pressure inhaler/volume inhaler disclosed herein to accurately calculate the amount of THC, CBD and/or other chemicals drawn up into the known volume of the device. Once calculated, the amount of medication, per draw, should be consistent throughout that batch of *Cannabis* oil produced and packaged into the cartridges. With this information, a physician can direct their patients to this device and know the amount of medication (THC, CBD, etc.) delivered per treatment. This will enable accurate labeling and proper instructions to users.

Embodiments of the positive pressure inhaler device consist of a modified hand pump with or without a separate holding chamber. The size and volume of the pump and chamber can be varied based upon use. Different chambers may be inserted onto the same pump when a separate chambers are used. The illustrations show a separate chamber has been added to the air intake end of a hand pump. This application includes the modification of a hand pump for medication delivery. Ultimately, the added chamber shown in these illustrations may be fully incorporated into the device.

In certain embodiments, a user may attach a holding chamber to the intake portion of a hand pump into which medication can be inserted or directly injecting the medication into the pump chamber. The holding chamber can serve as a manifold for the pump chamber. When a holding chamber is used it allows the suction of a hand pump to suction medication from a vaporization device such as a pMDI. Without a holding chamber, a port into the pump chamber allows the medication to be injected into the known volume of the pump chamber.

The holding chamber volume can be varied. For aerosol devices such as albuterol devices, the holding chamber is large enough to receive the initial dose of medication. Mediation is introduced into the either the holding chamber or pump chamber. When a holding chamber is used the opening of the pump chamber draws the drug-air mixture into the pump. Once the pump chamber is full, depression of the pump piston delivers the medication. Delivery can be slow and steady and is controlled by the operator of the device. The operator can imagine that he/she is pushing the medication into the lungs.

For *Cannabis*, the holding chamber size can vary or be non-existent. Total volume is either the pump chamber itself or the volume of the pump chamber cylinder plus the added holding chamber. As much medication is drawn into the pump chamber as possible. Dose is related to the size the pump chamber and the degree of suction generated by the pump and the amount of air, if any that is allowed to enter the pump chamber. The operator can use two stages. Initial draw takes in medication and the remaining draw brings air. For instance, the initial draw is ¼ of the entire pump chamber volume. The medication draw is then stopped and air is allowed into the chamber filling up the rest of the chamber. The air/medication mixture is then 3 to 1, but the dose of medication is determined by the initial draw.

Elements of the disclosed embodiments of the positive pressure inhaler generally include a cylinder of known volume to serve as the pump chamber, also referred to herein as the delivery chamber, a piston that moves up and down to draw material into the pump chamber and to expel material through the center rod of the piston, with or without a separable delivery chamber cap (or holding chamber) for introduction of medication into the delivery chamber, and accompanying valves to effect these actions. The positive pressure inhaler may also include a handle to move the piston up and down and a mouthpiece which can be part of the piston or affixed to the end of the piston. The delivery chamber or pump chamber—which is a chamber of known volume—is traversed, or partially traversed, with a piston to drive the air/medication mixture into the mouthpiece. In use, air is drawn up into the pump chamber, valves optionally seal the pump chamber, medication is added to the chamber and then expelled through one end of the delivery chamber, into the patient's lungs.

With reference to FIGS. 8-11, the elements of a first embodiment a positive pressure inhaler 8 include a cylinder 10 of known volume, a piston 12 that engages the interior side walls of the cylinder 10, and which travels at least part of the length of the cylinder 10. The known volume of the cylinder that is displaced by the motion of the piston 12 comprises a pump chamber 14. The piston 12 moves up and down to draw material into the pump chamber 14 and to expel material through the center rod 16 of the piston 12. A handle 18 may be integral to, or separately affixed to the piston 12, to enable a user to manually move the piston 12 up and down. A mouthpiece 14 may be part of the piston 12, for delivery of the material into the respiratory pathway of a patient using the positive pressure inhaler 8. The positive pressure inhaler 8 may also include a delivery chamber cap 16 which includes a holding chamber. The delivery chamber cap 16 may be integral to, or affixable to, the cylinder 10, to enable delivery of medication into the delivery chamber 14, using various approaches, as described further below. The cylinder 10, or the delivery chamber cap 16, include one or more valves for allowing a known amount of air inflow into the pump chamber 14.

An important aspect of the embodiments disclosed herein is the valve design to control inflow and outflow of air, into and out of the delivery chamber 14. A variety of different configurations are available and can be used with embodiments of the present invention, so long as the valve and pump configuration has very good control of air inflow into the piston and negative pressure in the cylinder is controlled, so that during delivery of the medication on the downstroke of the piston, a substantial amount of additional air is not drawn into the piston, thereby changing the known volume of air into which aerosol medication has been disbursed.

One such embodiment is to have the piston 12 move downward generating a negative pressure in the cylinder 10. This negative pressure is known based upon the movement of the piston 12 which is designed to allow control of the negative pressure. The negative pressure draws aerosol or vapor from the delivery cap 16 holding chamber into the cylinder 10. There should be some room between the piston 12 as it ascends to the top of the cylinder 10 so that the piston does not leave the cylinder 10 or dislodge the delivery cap 16. The design of the delivery cap holding chamber 16 needs to be separately designed depending upon the type of aerosol, medication, or vapor that is being used. The delivery cap 16 holding chamber can be eliminated with direct access of the vapor outflow directly into the delivery chamber 14. FIG. 11 provides two illustrations of a schematic of a delivery chamber cap 16, with variable size openings 20, 22 to allow for attachment of vape pens of various manufacture, or other vaporizer devices.

Embodiments disclosed herein may also include a separate control mechanism for measuring and controlling negative pressure in the cylinder. Knowing the negative pressure and the volume, a doctor, patient or user can measure the amount of medication delivered into the cylinder when it is fully opened and the piston is at the bottom of the stroke. Thus, it is possible to measure the amount of medication delivered by each brand of vape pen and each product used in that vape pen. We can also measure and demonstrate the dose of medication after each draw.

Figure 12:
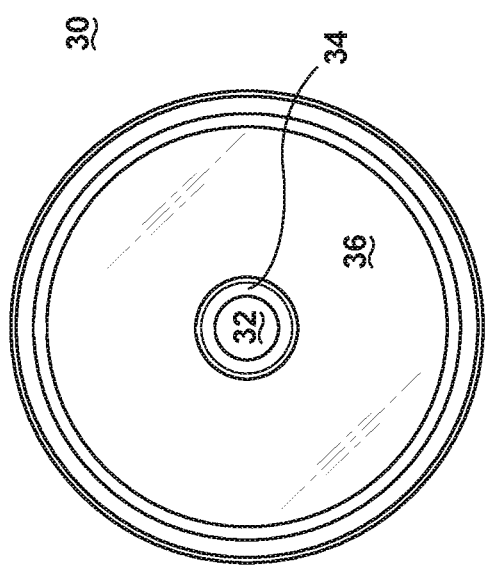
FIG. 12 is an illustration of a first embodiment a chamber cap of a second embodiment of the positive pressure inhaler, with the first embodiment of the chamber cap configured for allowing insertion and use of a conventional "510 thread" vape pen.
Figure 13:
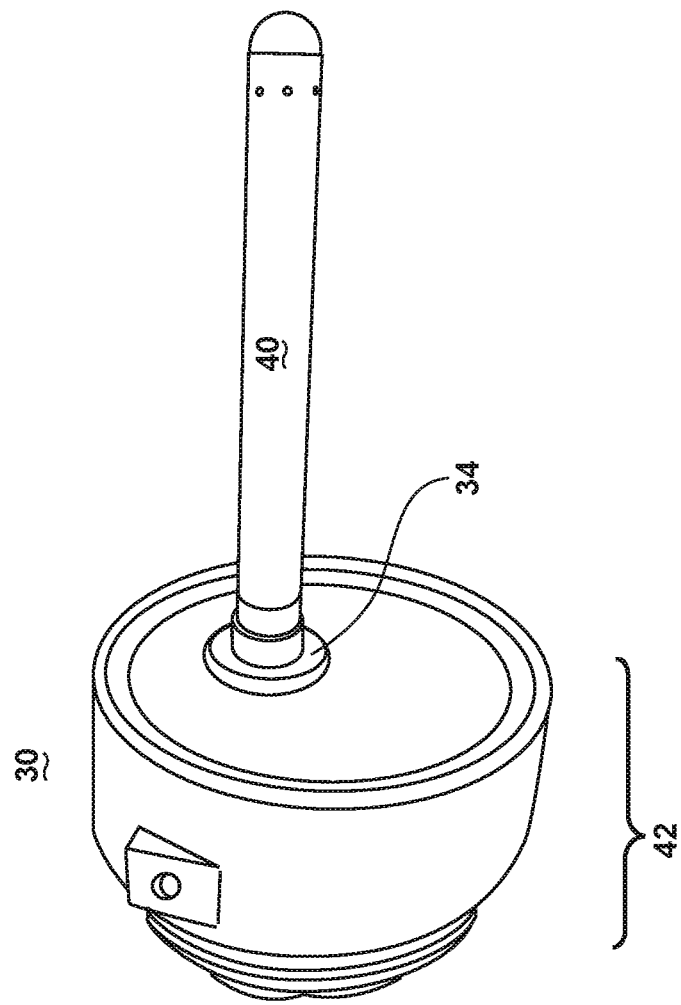
FIG. 13 is an illustration of the first embodiment of the chamber cap shown in FIG. 11, with a convention "510 thread" vape pen inserted in the chamber cap and substantially sealed into the chamber, for substantially airtight delivery of vaporized Cannabis into the delivery chamber.
Figure 14:
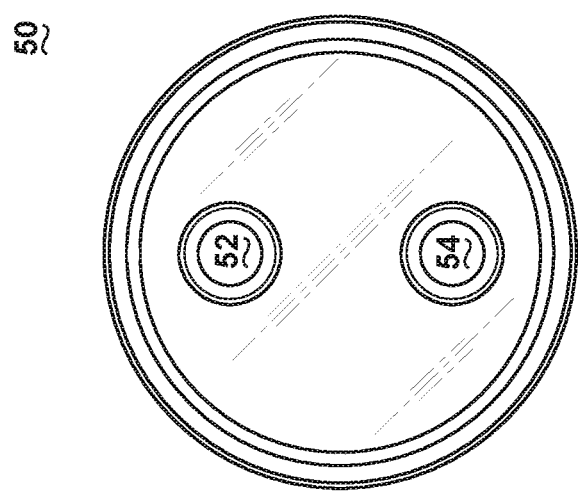
FIG. 14 is an illustration of a second embodiment of the chamber cap configured for allowing attachment of two conventional "510 thread" vape pens.

With reference to FIGS. 12-14, various embodiments of a delivery chamber cap or intake end of the cylinder can be configured for allowing insertion and use of a conventional "510 thread" vape pen are shown. FIG. 12 illustrates a top view of a delivery cap 30. The delivery cap 30 includes an aperture 32 defining an opening for inserting the mouthpiece of a vape pen. The aperture 32 further includes a rubberized gasket 34 for ensuring a substantially air-tight fit between the aperture and the mouthpiece of a vape pen, so as to reduce or eliminate the possibility of inflow of air that does not contain medication or vaporized *Cannabis*. Other affixation structures may also be used, including threads or collets, so long as a substantially air-tight connection is made between the delivery cap 30 and the vape pen. The delivery cap 30 may include a translucent or transparent pane 36 to allow a user to verify that *Cannabis* vapor (which is typically white) is present in the holding chamber of the delivery cap 30.

With reference to FIG. 13, the delivery chamber cap 30 of FIG. 12 has been outfitted with a vape pen 40, by inserting the mouthpiece (not shown) of the vape pen 40, into the aperture, making a substantially air-tight fit. It should be noted that the depth 42 of the delivery chamber cap 30 is such that it can serve as a separate holding chamber that is operatively connected to a delivery chamber. Alternatively, the delivery chamber cap 30 may be open and simply connectable to a delivery chamber.

With reference to FIG. 14, an alternative embodiment of the delivery chamber cap 50 is shown, with two apertures 52, 54, configured for allowing attachment of two conventional "510 thread" vape pens. As many openings can be used as space allows. This alternative configuration may be useful when a doctor or user wants to deliver a higher concentration of medication per the known volume than is otherwise achievable using a single vape pen.

Figure 15:
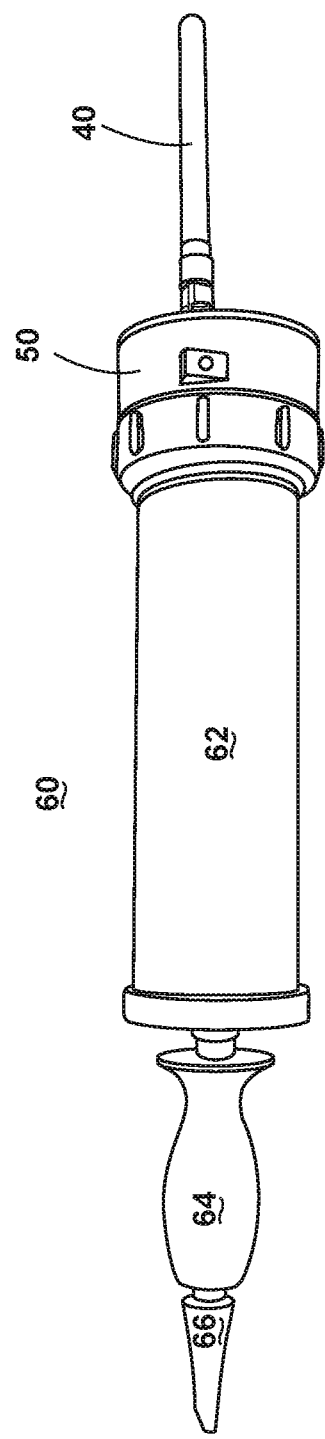
FIG. 15 is an illustration of a second embodiment of the positive pressure inhaler, configured with a vape pen chamber cap, and with a conventional vape pen extending therefrom.

With reference to FIG. 15, a second embodiment of the positive pressure inhaler 60, configured with the vape pen chamber cap 50 of FIG. 13, and with a conventional vape pen 40 extending therefrom, is shown. The positive pressure inhaler 60 includes a cylinder 62, containing a known interior volume serving as a delivery chamber (not shown). A piston (not shown) is in a compressed position in the delivery chamber. A handle 64 is integral to the piston rod, and a mouthpiece 66 is integral to the distal end of the piston rod.

As discussed, certain embodiments are configured to provide a "double-action," so that each travel of the piston result in both an inflow of aerosolized/vaporized medication on one side of the piston, as well as a displacement of aerosolized/vaporized mediation on the other side of the piston. Specifically, in certain embodiments, the piston operably divides the pump chamber into a first section and a second section (not shown). The inflow valve is operably connected to the first section of the pump chamber and the outflow valve is operably connected to the first section of the pump chamber. Further, a secondary inflow valve is operably connected to a second section of the pump chamber and a secondary outflow valve operably connected to the second section of the pump chamber and the patient delivery port. The pump chamber, the piston, the inflow valve, the outflow valve, the secondary inflow valve and the secondary outflow valve are configured such that upon the second traversal of the piston through the pump chamber and while the aerosolized/vaporized medication is displaced from the first section of the pump chamber and through the patient delivery port, a second dose of aerosolized/vaporized medication will be drawn through the secondary inflow valve into the second section of the pump chamber.

Then, upon a third traversal of the piston through the pump chamber, and while the second dose of aerosolized/vaporized medication is displaced from the second section of the pump chamber and through the patient delivery port, a third dose of aerosolized/vaporized medication will be drawn through the inflow valve into the first section of the pump chamber.

Figure 16:
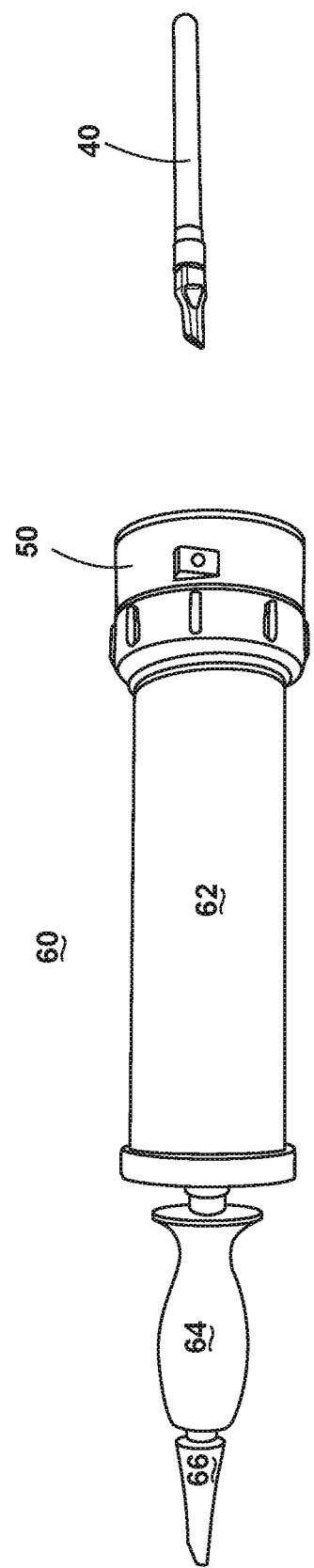
FIG. 16 is an illustration of the second embodiment of the positive pressure inhaler, configured with a vape pen chamber cap, but with the conventional vape pen removed therefrom.

With reference to FIG. 16, the vape pen has been removed from the vape pen chamber cap.

Figure 17:
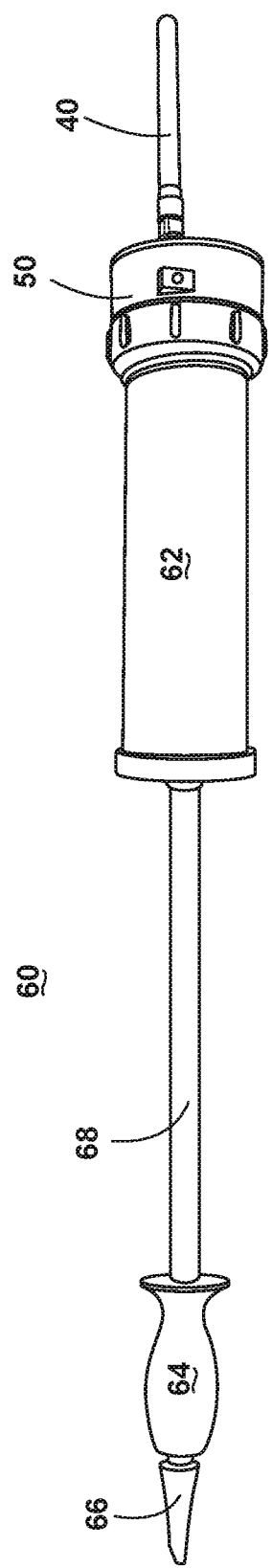
FIG. 17 is an illustration of the second embodiment of the positive pressure inhaler, configured with a vape pen chamber cap, and with a conventional vape pen extending therefrom, and further with the piston extended to its furthest extent.

With reference to FIG. 17, the piston has been drawn to its extended position and the piston rod 68 is visible. By moving the piston to this position, the piston has created negative pressure on the mouthpiece of the vape pen 40 and caused it to vaporize *Cannabis* oil. This vapor has resultantly been drawn into and dispersed throughout the known interior volume of the delivery chamber inside the cylinder 62. The positive pressure inhaler is now ready for a user to move the piston in a downstroke to cause the vaporized *Cannabis* oil in the delivery chamber to be driven, with positive pressure, through the hollow stem of the piston rod 68, and out through the mouthpiece 66, and thus into a user's respiratory tract. (See FIGS. 24-29).

Figure 18:
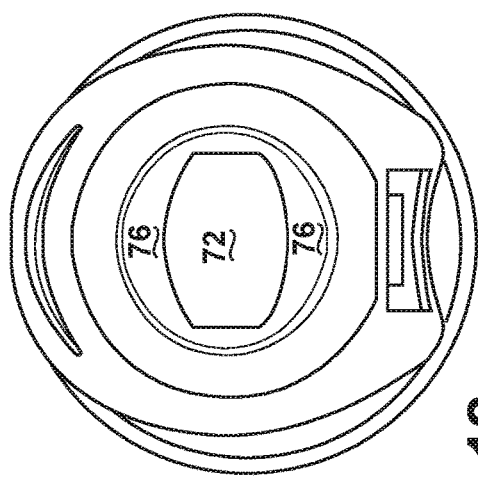
FIG. 18 is an end-on exterior illustration of a third embodiment of a chamber cap of the second embodiment of the positive pressure inhaler, with the chamber cap configured to allow insertion of the mouthpiece of a prior art pMDI.
Figure 20:
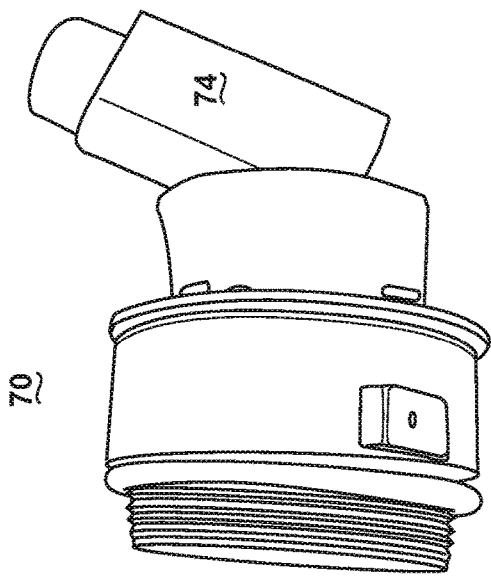
FIG. 20 is a side-on exterior illustration of the third embodiment of the chamber cap shown in FIG. 16, with the prior art pMDI inserted into the cap.
Figure 19:
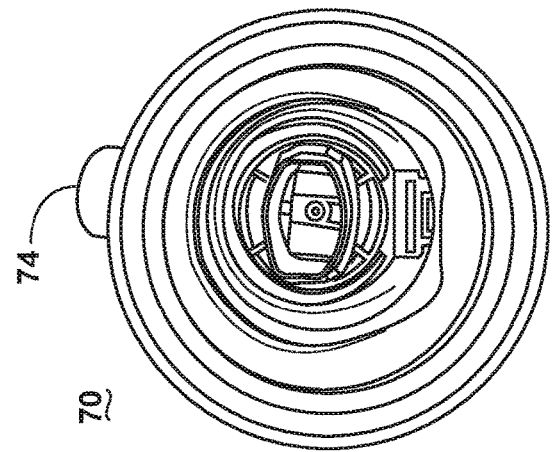
FIG. 19 is an end-on interior illustration of the third embodiment of the chamber cap shown in FIG. 16, with a prior art pMDI inserted into the cap.
Figure 21:
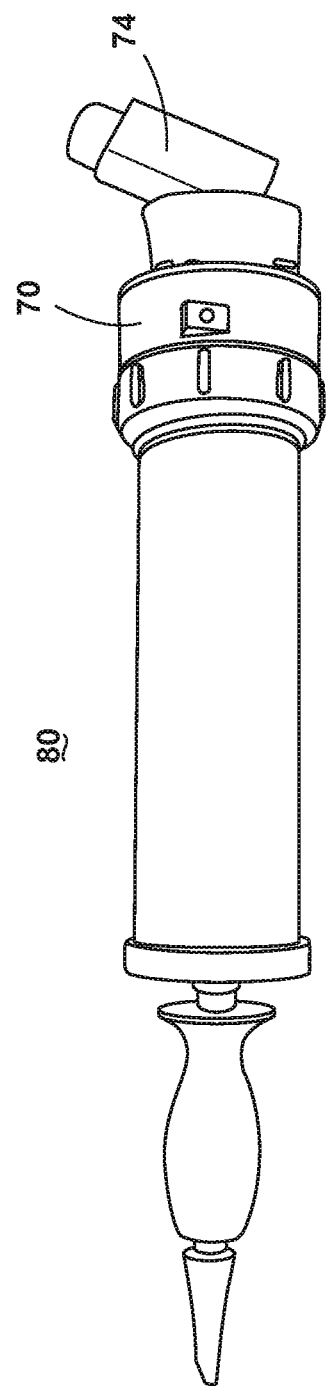
FIG. 21 is a side illustration of the second embodiment of the positive pressure inhaler, with the third embodiment of the chamber cap in place, and with a prior art pMDI inserted into the cap.

With reference to FIGS. 18-20, an alternative embodiment of a delivery chamber cap 70 for use with a pMDI is shown. The delivery chamber cap 70 includes a threaded cap 72 for connection to a delivery chamber of a positive pressure inhaler 80, such as is shown in FIG. 21. The delivery chamber cap 70 includes an aperture 72 configured for insertion of the mouthpiece of a pMDI 74. The aperture 72 is preferably formed by a rubberized gasket or membrane 76, which forms a substantially air-tight connection between the mouthpiece of the pMDI 74 and the delivery chamber cap 72, so as to prevent inflow of unwanted air into the known volume of the delivery chamber (not shown).

With reference to FIG. 21, the third embodiment of the delivery chamber cap 70 shown in FIGS. 18-20 is affixed to the positive pressure inhaler 80, with a prior art pMDI 74 inserted into the aperture of the cap 70 and held in substantially air-tight communication with the inhaler 80.

Figure 22:
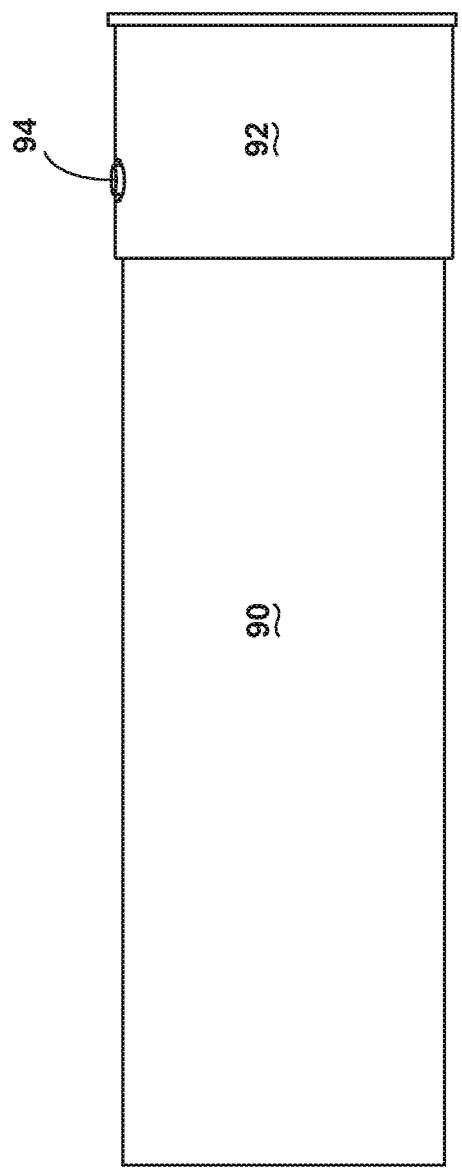
FIG. 22 is an illustration of a fourth embodiment a chamber cap of the second embodiment of the positive pressure inhaler, with the fourth embodiment of the chamber cap configured for allowing insertion and use of a prior art canister and metering valve as would be used with a prior art pMDI, but without the prior art actuator and mouthpiece.
Figure 23:
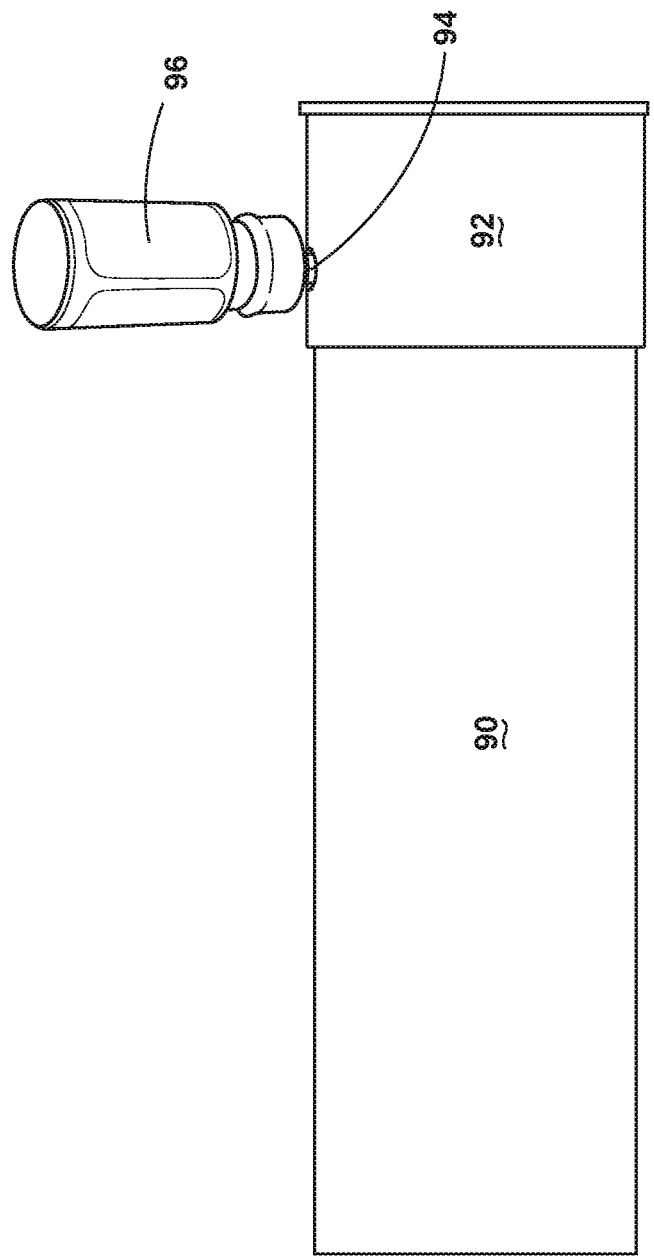
FIG. 23 is an illustration of the fourth embodiment of the chamber cap of FIG. 20, with a prior art canister and metering value in operative connection to the cap, such that at least a portion of the stem of the metering valve is inserted into the chamber cap.

With reference to FIGS. 22-23, an alternative embodiment of the positive pressure inhaler cylinder 90, with an alternative embodiment delivery chamber cap 92 is shown, for allowing insertion and use of a prior art canister and metering valve as would be used with a prior art pMDI, but without the prior art actuator and mouthpiece. Opening the piston allows the canister to be filled with medication injected into a known volume of air. The delivery chamber cap 92 may be integral to, or removably affixed to, the cylinder 90. The delivery chamber cap 92 is configured to enable delivery of aerosolized medication into the delivery chamber via a port 94 for insertion and activation of the stem of a prior art canister and metering valve 96, such as is typically used with a pMDI for delivery of Albuterol. The port 94 preferably includes a rubberized gasket that contacts the metering valve stem and creates a substantially air-tight connection. In use, once the metering valve stem is inserted into the port 94, the prior art canister and metering valve 96 can be depressed in the same way that it would be used if it was a part of a complete pMDI. Upon depression, a single dose of the pressurized medication in the canister 96 is aerosolized into the delivery chamber of the cylinder 90, for eventual delivery to a patient as described herein.

Figure 25:
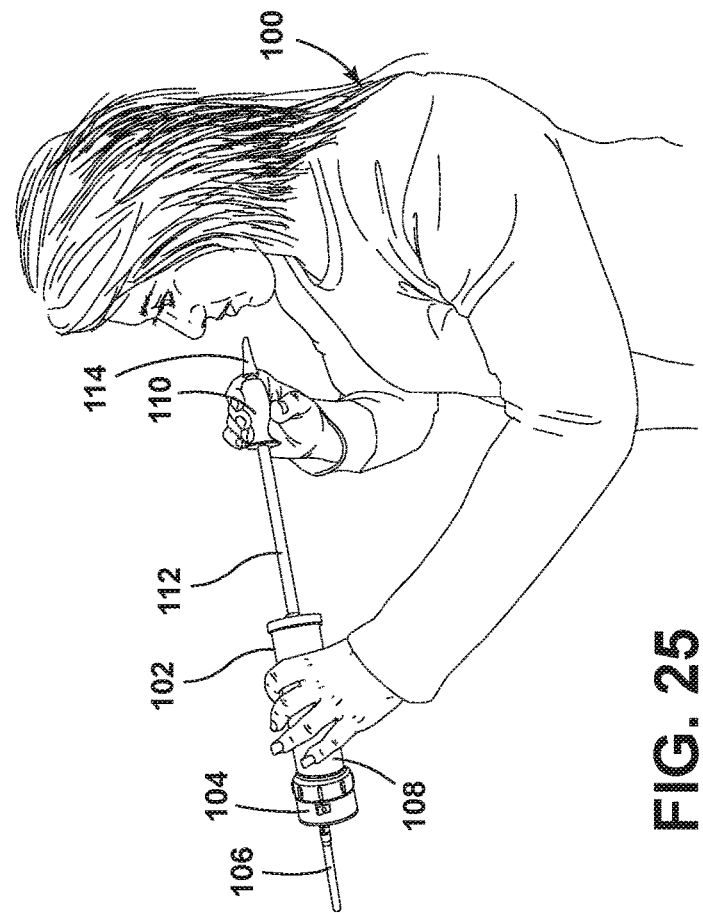
FIGS. 24-27 are illustrations of steps taken by a patient to use the second embodiment of the positive pressure inhaler, configured with the vape pen chamber cap.
Figure 24:
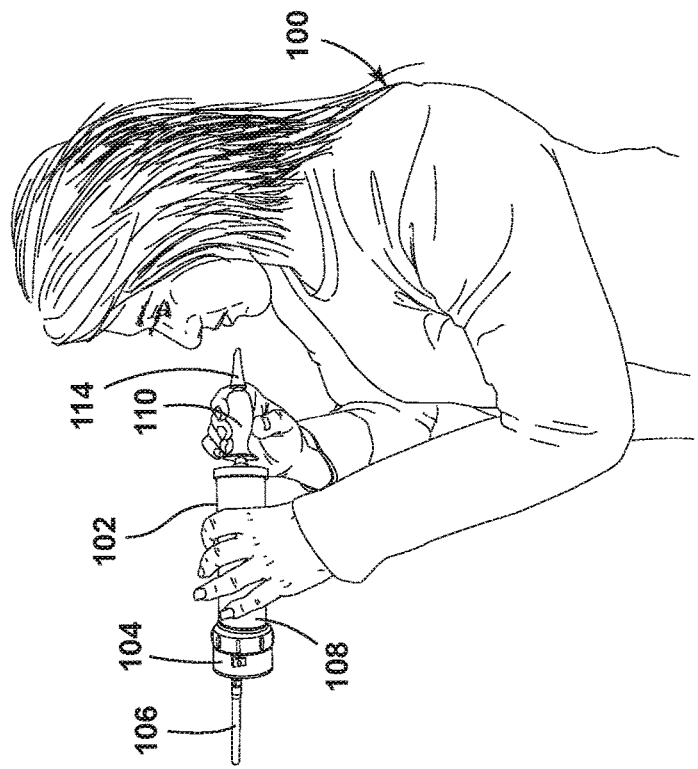
Figure 26:
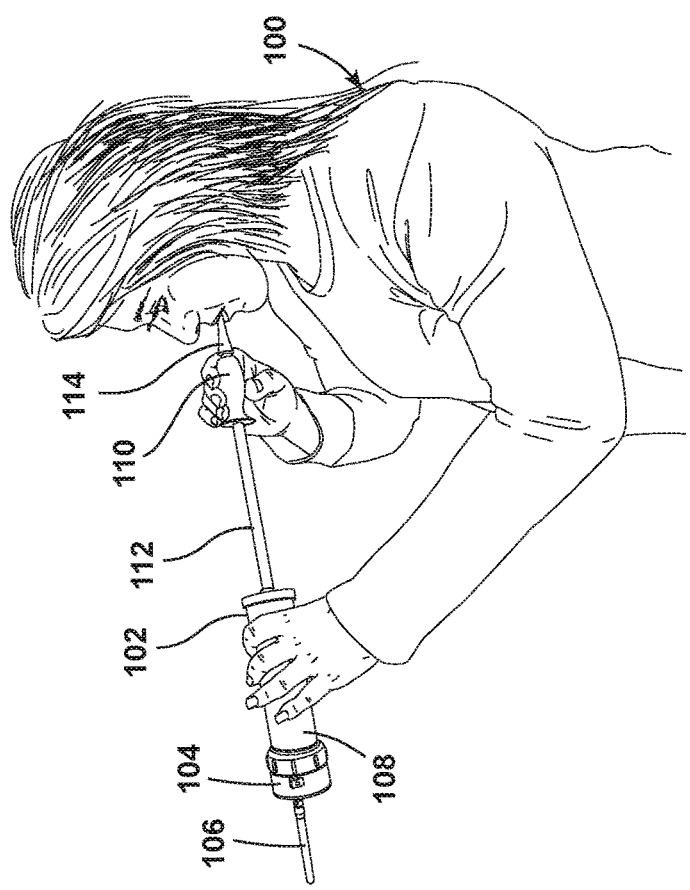
Figure 27:
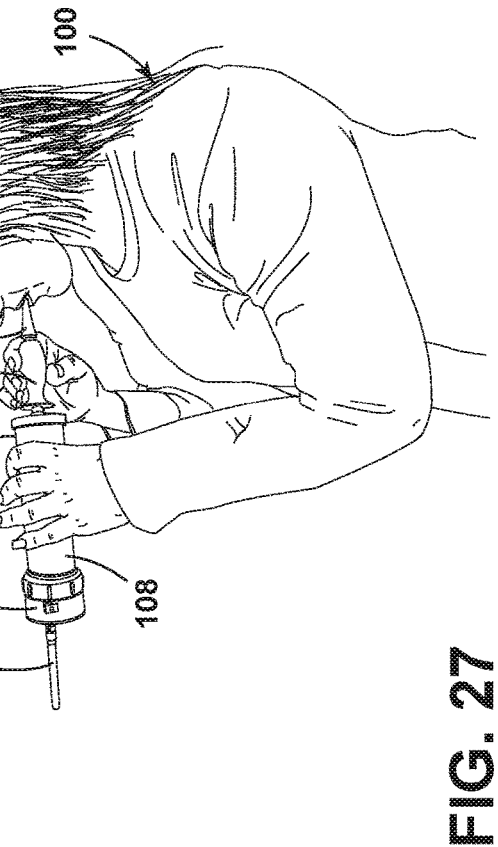

With reference to FIGS. 24-27, two alternative methods of use of embodiments of the positive pressure inhaler are shown. In FIGS. 24-27, a patient 100 is using an embodiment of the positive pressure inhaler 102, configured with the vape pen delivery chamber cap 104, to consume vaporized medical *Cannabis*. In FIG. 24, the patient 100 positions the vape pen 106 in the aperture of the vape pen delivery chamber cap 104 and prepares to use the device by grasping the cylinder 108 and the handle 110. In FIG. 25, the patient 100 uses the handle 110 to draw the piston 112 forward, thereby creating negative pressure on the vape pen 106 mouthpiece and causing it to vaporize *Cannabis* oil and deliver the vaporized *Cannabis* oil into the known volume of the cylinder 108, through the delivery chamber cap 104. In FIG. 26, the patient 100 closes her lips around the mouthpiece 114, creating a substantially air-tight seal, and prepares to inhale. In FIG. 27, the patient 100 simultaneously inhales while drawing the cylinder 108 toward the mouthpiece 114, thereby moving the piston 112 through the known volume of the cylinder, which contains vaporized *Cannabis* oil from the step shown in FIG. 25. As a result of this action, the vaporized *Cannabis* oil and the known volume of air is driven, with positive pressure, into the patient's respiratory tract. As explained above, the patient 100 may use as many inhalatory breaths as needed to drive the entire known volume of air and vaporized *Cannabis* oil into her lungs. By doing so, the patient will receive a measured dose of vaporized *Cannabis* oil, regardless of the number of breaths needed due to her lung capacity or a coughing response to delivery of the vaporized *Cannabis* into her lungs. This process will work for any vaporized, aerosolized or gaseous medication introduced into the cylinder 108.

Figure 28:
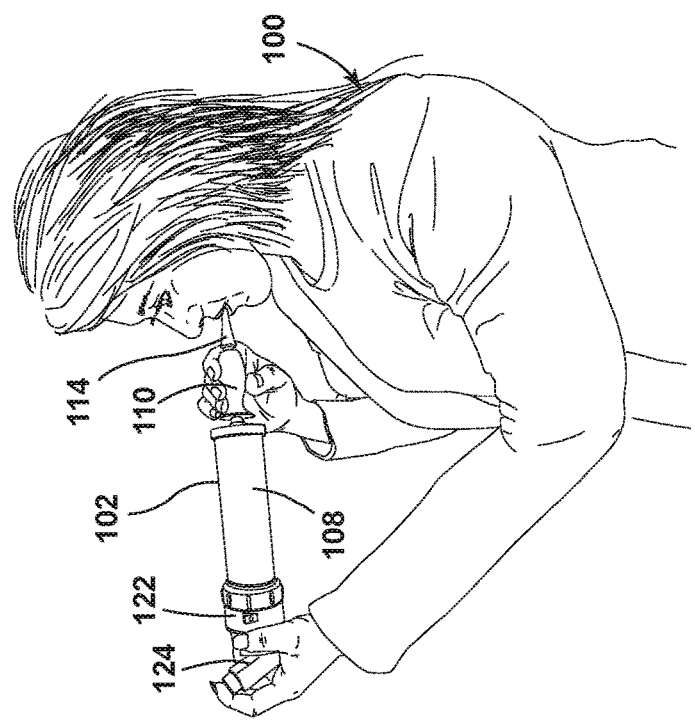
FIGS. 28-29 are illustrations of steps taken by a patient to use the second embodiment of the positive pressure inhaler, configured with the pMDI accessible chamber cap.
Figure 29:
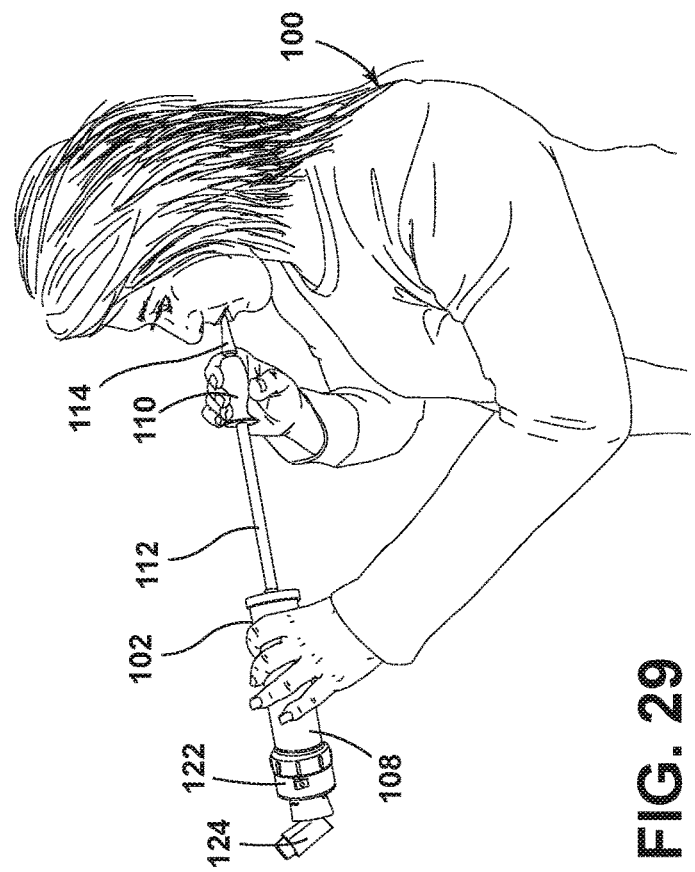

With reference to FIGS. 28-29, a patient 100 is using an embodiment of the positive pressure inhaler 120, configured with the pMDI delivery chamber cap 122, to deliver Albuterol from a prior art pMDI 124. Steps necessary to deliver Albuterol are similar to those described above, with the extra step of the patient activating the pMDI by depressing the pMDI canister to deliver the aerosolized Albuterol into the delivery chamber, as shown in FIG. 28.

Figure 30:
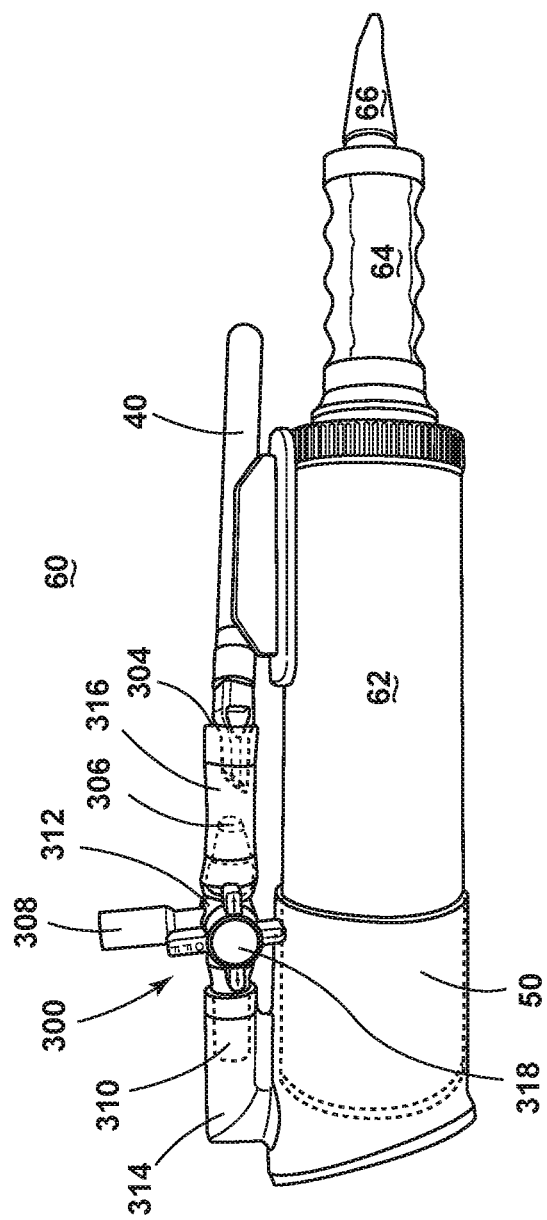
FIG. 30 is an illustration of a third embodiment of the positive pressure inhaler, with an inflow port valve enabling a user to change the medical device from which medication, gas, or air flows into the inflow valve and thus to the pump chamber, with a 510 thread vape pen attached to the inflow port valve primary inflow port and the pump handle/patient mouthpiece in an extended position after a first traversal of the piston.
Figure 31:
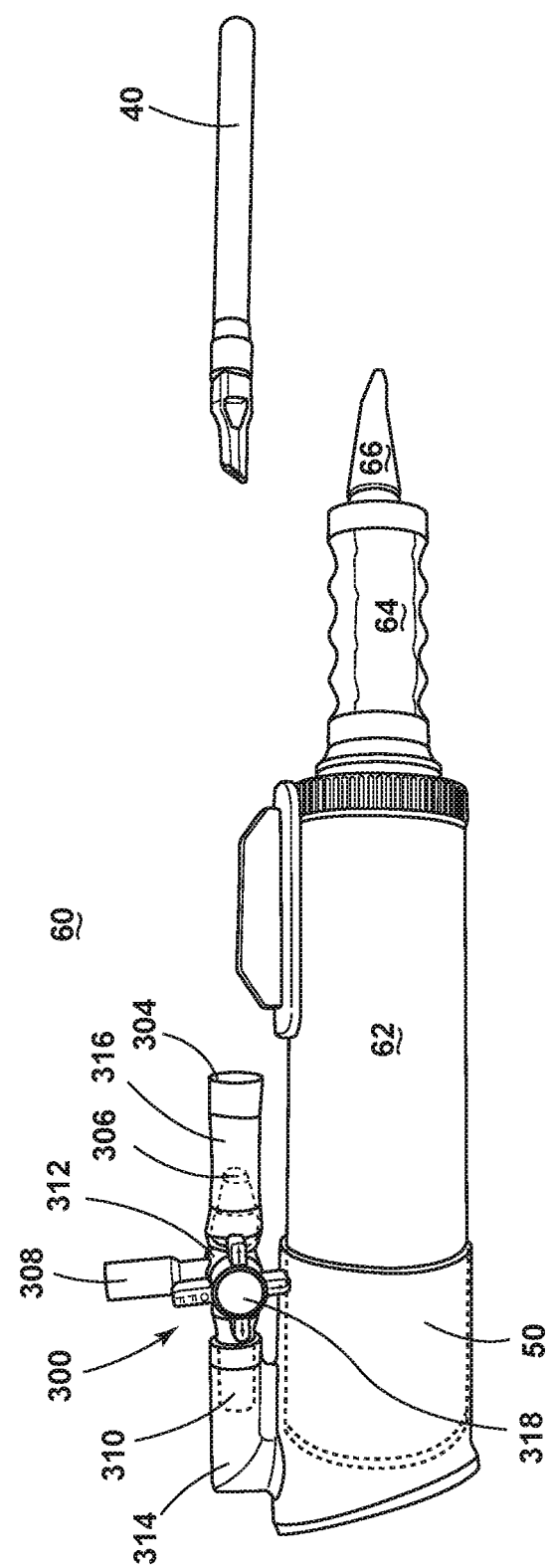
FIG. 31 is an illustration of the third embodiment of the positive pressure inhaler, with an inflow port valve enabling a user to change the medical device from which medication, gas, or air flows into the inflow valve and thus to the pump chamber, with a 510 thread vape pen detached from the inflow port valve primary inflow port.
Figure 32:
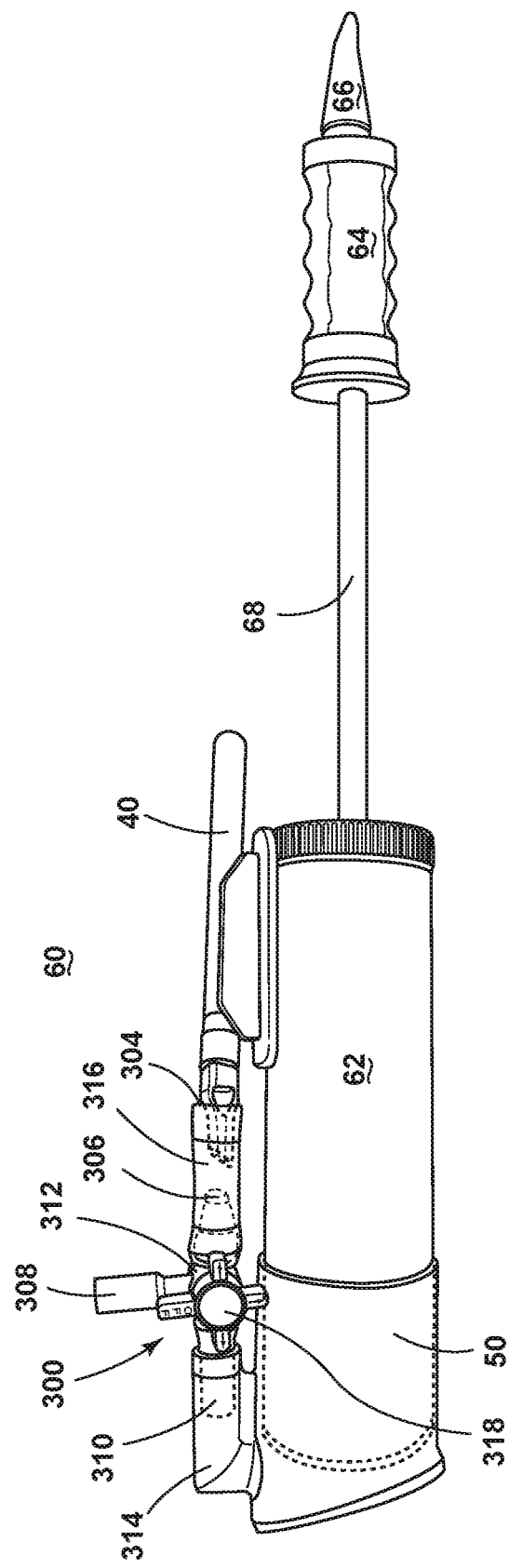
FIG. 32 is an illustration of the third embodiment of the positive pressure inhaler, with an inflow port valve enabling a user to change the medical device from which medication, gas, or air flows into the inflow valve and thus to the pump chamber, with a 510 thread vape pen attached to the inflow port valve primary inflow port and the pump handle/patient mouthpiece in a compressed position after a second traversal of the piston.

With reference to FIGS. 30-32, a third embodiment of the positive pressure inhaler 60 is illustrated and is similar to prior discussed embodiments. The holding chamber 50 (which is also referred to herein as a "manifold") may be affixed to the cylinder 62 either removably or permanently, so long as the holding chamber and the interior of the cylinder 62 are in a gas-tight communication. For example, the holding chamber 50 may be threadably attached to the cylinder 62, or it may be attached by adhesive, or it may be integral to the cylinder 62. The third embodiment has a separate inflow port valve 300 and a 510 thread vaporizer pen rest 302 on which the vape pen 40 may be rested an secured when the vape pen 40 is inserted into the inflow port 304. The inflow port valve includes an inflow valve primary inflow port 306, an inflow valve discretionary inflow port 308, an inflow port valve outflow port, and an inflow port valve member (not shown) inside the valve body 312. The inflow valve outflow port 310 is operably connected to the pump chamber inflow valve (not shown) by an airtight conduit 314. The inflow valve primary inflow port 306 is operably connected to the inflow port 304 by a similar airtight conduit 316. The inflow port valve member is configured such that actuation of the inflow port valve member, by the inflow port valve handle 318 switches between a first position that enables flow from the inflow valve primary inflow port 306, and a second position that enables flow from the inflow valve discretionary inflow port 308. As pictured in FIG. 30, the valve handle 318 and the valve member are in the first position to enable flow from the inflow valve primary inflow port 306, to which the vape pen 40 is operably attached. In FIG. 30, the valve member is positioned such that the inflow valve discretionary inflow port 308 is closed. As shown in FIG. 32, the pump handle 64 may be drawn so that the piston (not show) traverses the pump chamber, creating negative pressure to draw in aerosolized/vaporized medication from the vape pen 40.

In some embodiments, and as shown in FIGS. 30-32, the inflow valve discretionary inflow port 308 is operably connected to an opening to the atmosphere, so that, upon actuation of the valve member, a first defined volume of air may be introduced into the pump chamber by negative pressure to dilute the first defined volume of aerosolized/vaporized medication that has already been drawn into the pump chamber by a partial traversal of the piston, e.g., a draw of only ⅓ of the piston length from the inflow valve primary inflow port 306, and a draw of ⅔ the piston length from the inflow valve discretionary inflow port 308. Alternatively, the inflow valve discretionary inflow port 308 may be operably connected to a discretionary medical device (not shown) such as an oxygen canister, a second pMDI, a nebulizer, etc., so that a second volume of a gas or aerosolized/vaporized medication may be introduced into the pump chamber by negative pressure to dilute the first defined volume of aerosolized/vaporized medication. Additionally, the ports of the inflow port valve may be utilized to deliver a different medication on each stroke of the piston, in order to provide multi-step treatments Examples include, but are not limited to: (a) an aerosolized delivery of lidocaine to numb the patient's cough reflex, followed by delivery of a pulmonary medication that would otherwise induce coughing; (b) aerosolized fentanyl for immediate systemic pain relief to a patient at the scene of an accident, followed by oxygen; or (c) oxygen, followed by an aerosolized delivery of CBD. Further, it should be understood that while an inflow port valve with two inflow ports has been described, an inflow port valve with any necessary or convenient number of inflow ports is contemplated and included in this disclosure. Moreover, while the valve member described with respect to FIG. 30-32 is a ball valve, it should be understood than any suitable valve type may be used, including mixing valves that allow inflow from both ports, in a specified ratio, at the same time.

A further discussion of alternative embodiments and methods is as follows. Embodiments of the positive pressure inhaler include the addition of a closed pump chamber into which medication and/or other products are injected or inserted. (See FIG. 23). One such other product is medicated powder for inhalation deliver, such as those used for dry powder inhalers ("DPI"). The chamber is used to hold and deliver medication into the oral airway under the operator's control.

For aerosols such as Albuterol, a port at the back of the hand pump is added which empties into a chamber. (See FIG. 23) When the pump chamber is opened up to a specified volume, the aerosol is drawn into the chamber and the pump is depressed pushing the medication into the lungs. Alternatively the aerosol can be delivered directly into the open pump chamber.

Embodiments of the positive pressure inhaler lends itself to a method of adding medication, smoke, aerosolized powder, aerosolized liquid, or other aerosolized products into a chamber immediately adjacent to the intake portals of a manual pump or portable (self-contained) electronic pump. When the plunger of the pump is initially activated it sucks the aerosolized product from a delivery devise immediately adjacent to the intake portal into the pumping system. The exact volume of air/medication is controlled and reproducible. Concentration of the medication is controlled by the volume of air added to the air/medication mixture. Alternatively the material can be drawn directly into the pump chamber.

Once the pumping plunger is depressed the air in the pump chamber is forced through the central canal of the piston/plunger for inhalation.

The patient is informed that by depressing the piston/plunger he is pushing air/medication into the lungs. Piston/ plunger depression controls the rate of inhalation and the patient does not have to listen to a noise, or look at a meter to know the rate of inhalation. The pump can be manually or electronically driven.

Embodiments of the positive pressure inhaler may include various options and additions, such as a flow rate indicator, based on travel of plunger. In certain embodiments, multiple medications can be added into chamber through one port or multiple ports. Similarly, different gasses can be added into the chamber, when the chamber is closed once the piston/plunger starts to move.

In some embodiments, there may be adjustable stops on the piston/plunger or pump chamber to control the amount of medication drawn into the chamber. A light or sound or other notification can let the user when he has reached a certain volume or percentage of the device's holding capacity (10 ml or 10% of the total pump chamber capacity or a certain dosage of medication).

Airflow is controlled by the design of the piston/plunger and the intake portals.

Detachable mouth pieces can be used for hygiene and control of outflow.

Holding chambers may be used which are disposable, or which are pre-loaded with medication. Further, the design of the piston may be augmented to include a puncture or crush device, so that the travel of the piston to its full length causes a pre-loaded medication holding chamber to be punctured, or a tablet to be crushed to powder, so that the second stroke of the piston aerosolizes the pre-loaded medication or crushed powder in the pump chamber through application of negative pressure.

For *Cannabis* vapor the dosage of each stroke of the pump—for a given model of vape pen—can be calibrated by measuring the by number of strokes of the hand pump to empty a container of a known volume of *Cannabis* oil. Dividing the amount of medication by the number of strokes to empty the container gives you the dose per pump. Alternatively, the concentration of *Cannabis* or medication can be calculated from the smoke itself or by distilling the *Cannabis* out of the smoke contained in the canister. (When an Albuterol inhaler is used, for example, the dose of the medication is determined by pressing the canister into a receptacle, this is not possible with most medication.)

Other delivery chamber caps may be used or developed to enable delivery of other medications, or more convenient delivery of known forms of medication, particularly with respect to known delivery devices, such as current balloon pups or holding chambers. Delivery chamber caps may also include detachable backs for different types of medication. Adding a screw back (or other locking mechanism) to the current balloon pumps to allow attachment of a chamber is also an option. Attachments can be disposable or reusable. A contained amount of medication can be loaded into the chamber.

Chambers can be changed for different medication or strengths of medication. Based on the amount of outside air that is allowed to enter the pumping chamber the concentration of medication can be controlled.

Attaching a system to the pump chamber that allows the user to know the volume of medication taken into the system. Notification can be by sound, light or other method. When the pump chamber has a known volume or a percentage of the chamber filled with medication the user can stop medication flow into the chamber and continue to draw air into the chamber diluting the concentration of medication in the chamber. He can control the concentration of a medication to avoid respiratory irritation.

In one example of use, a positive pressure inhaler can be configured as either a single use device, or a multi-use device with a single use delivery cap that is pre-loaded with a pain medication that can be aerosolized, such as Fentanyl. When a paramedic arrives at the scene of a patient in severe pain, the paramedic can have the patient inhale the medication giving immediate relief.

For aerosols, such as Albuterol or Mometasone, the delivery chamber is opened to the desired volume. The aerosol is injected into the chamber. The exact amount and concentration of medication is known. The patient inhales at his own rate and can force the mediation into his airway. Effectiveness can be enhanced by pinching the nostrils. The rate of inhalation is not critical. The number of breadths is not critical. Only the volume of medication is critical. The unit can be self-contained and loaded for one or more dosages of medication. Depression of a trigger injects one dose of medication into the chamber.

Some embodiments may include an anti-blowback valve to prevent a patient from pushing air back into the delivery chamber through the mouthpiece. This also would allow the positive pressure inhaler to be used from session to session without contamination of the chamber by different patients. The mouthpiece needs to be cleaned or disposable.

Control of inflow and outflow of air from chambers of pump may be controlled by the size of the inflow and outflow openings, and/or by valves, which may be adjustable or non-adjustable, mechanical or electrical.

Certain embodiments of the positive pressure inhaler may include a delivery chamber cap configured for use with a nicotine vaporizer or e-cig, so as to control the exact amount of nicotine in each session, thereby enabling a patient to accurately dose nicotine (in ever smaller amounts) as part of a program of detoxification and withdrawal from Nicotine addiction.

Certain embodiments of the positive pressure inhaler may include a delivery chamber cap configured for a cigarette attachment to allow use of chamber with a cigarette or a *Cannabis* "pre-roll".

Various terpenes and other chemicals have been used in aroma therapy. Certain embodiments of the positive pressure inhaler will allows precise dosage of terpenes, vaporized essential oils and other aromatherapy vapors to enable research on the best dosage and combination of chemicals.

In certain embodiments of the positive pressure inhaler, the delivery chamber cap may be a vaporizer in and of itself. For example, the delivery chamber cap may include a battery, a cartomizer and a fluid chamber that is prefilled with *Cannabis* oil, medication, or nicotine vaporizer fluid. The entire delivery chamber cap is disposable or reusable once the medication has been dispensed. The battery can be rechargeable.

In a different configuration of the positive pressure inhaler, the delivery chamber can be prefilled with *Cannabis* oil of a known concentration. The vaporization device is left attached to the chamber and when the patient draws through the chamber he receives doses from the smoke in the chamber and the additional vapors from the attached vaporization device.

Other embodiments of the positive pressure inhaler can include multiple holding chambers, each holding a different medication, such that each full travel of the piston can trigger additional medication delivery into the delivery chamber. These embodiments are configured for use with medication which may require a number of pumps to get the full dose or which require sequential dosing of medication. For example, a pretreatment with lidocaine can be the first dose of the inhalation agent, before a dose of subsequent asthma medication. The unit can be self-contained. In other variations of these embodiments, a fixed number of passes with the piston, e.g., five passes of the pump, with the first medication triggers the release of the second medication. Medication release then stops when the full dose of each medication is delivered.

In other embodiments, attaching a tube inflow would allow dosages which are larger than the delivery chamber volume. A nebulizer could provide initial lidocaine for anesthetic prior to medication administration. Oxygen or other gasses can be used to fill the chamber if needed or desired.

In a fully automated system, the positive pressure inhaler has controls for volume and concentration which could be programmed. If the cartridge composition is noted, the dose of medication would be calculated and delivered into the chamber along with enough air or other gas to dilute the medication to a known concentration to avoid respiratory irritation. Further, in a fully automated version, the height, weight, surface area and any other medical parameter of the patient can be programmed into the delivery system. The delivery system can then dispense the amount of medication into the delivery chamber allowing very accurate dosing based on patient medical parameters. Furthermore, research using such a devise can determine best dosages for users.

Further, using embodiments described herein, the exact amount of *Cannabis* or other medication can be known. Research can be done on the effects of the more than 100 cannabinoids in *Cannabis*.

Figure 33:
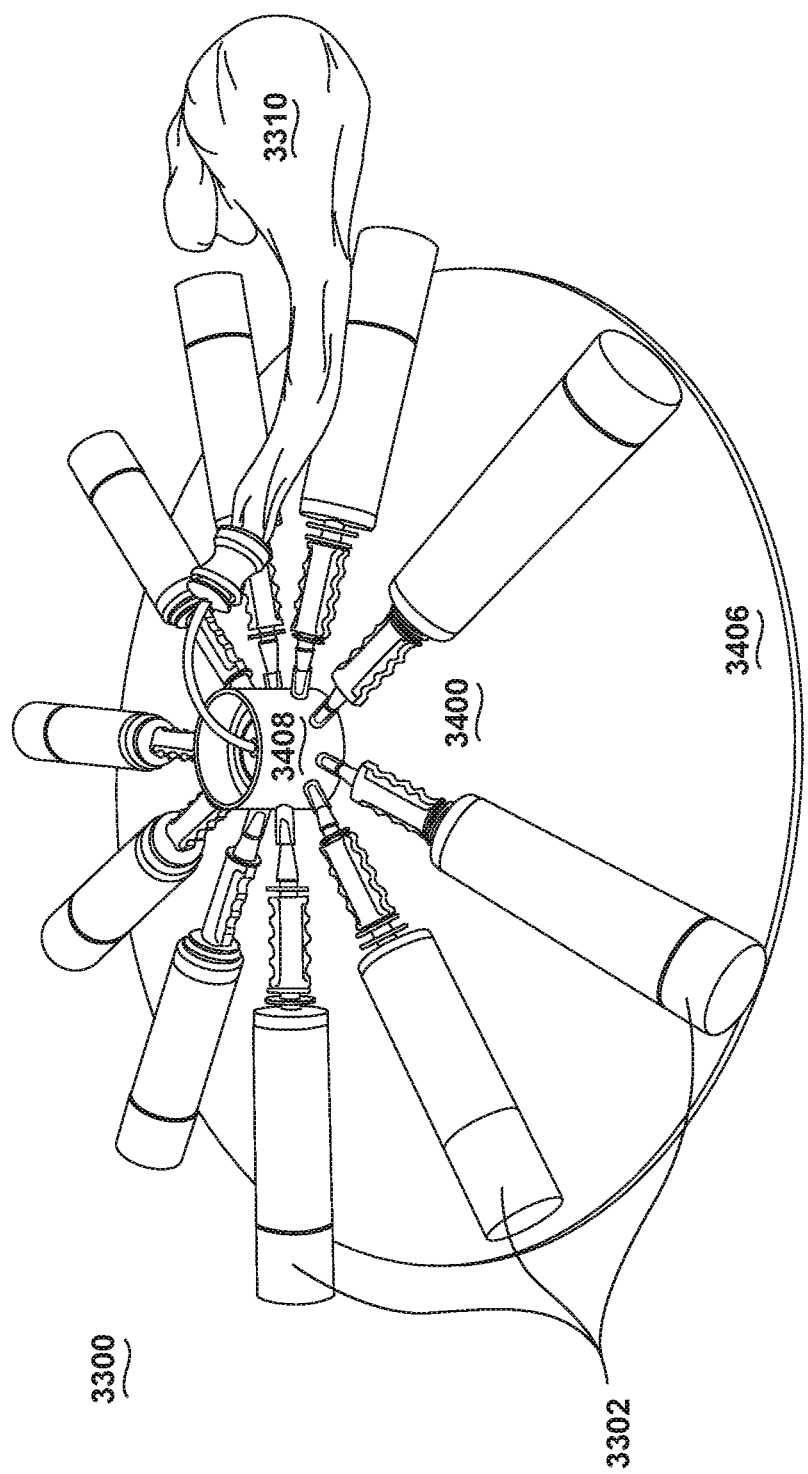
FIG. 33 is a schematic illustration of a testing assembly for testing the volume and quantity of aerosolized/vaporized medication.

With reference to FIG. 33, a aerosol/vaporizer medication dosage testing system 3300 is provided. The system includes a plurality of positive pressure inhalers 3302 of any one of the embodiments discussed herein. The system also includes a volumetric testbed 3304 that has a support table 3306 on which the plurality of positive pressure inhalers 3302 are mounted, a receiver valve 3308 (also referred to herein as a manifold), which is in airtight communication with each of the patient delivery ports of each of the plurality of positive pressure inhalers 3302, and a capture vessel 3310. In the embodiment shown, the capture vessel 3310 is an inflatable balloon, but it can be any suitable device for capturing and/or measuring gas volume and the concentration of aerosolized/vaporized medication or particulates in the gas volume delivered from the receiver valve 3308. The receiver valve 3308 is in airtight communication with the capture vessel 3310, configured such that, upon traversal of each of the respective pistons of each of the plurality of positive pressure inhalers 3302, the respective aerosolized/vaporized medication of each of the positive pressure inhalers is displaced through the receiver valve 3308 and into the capture vessel 3310. As illustrated, the system is configured for ten positive pressure inhalers, but it could be configured for any convenient number.

The system enables testing of the concentration/quality of any aerosolized/vaporized medication devices attached to the plurality of positive pressure inhalers. It is widely believed that a "first draw" from most 510 thread vaporizers delivers a lower concentration/lower quality vapor than subsequent draws, due to the configuration of most cartomizers/batteries which impacts the time that is required for the cartomizer to heat up and the resulting amount of *Cannabis* oil that is aerosolized/vaporized. For recreational consumers of *Cannabis* oil, dosage variation may be impactful, but is not critical. However, for medical treatment, quantifying the dosage from a given treatment is important, so the ability to test and gather data regarding concentration and quality of the vapor delivered by different 510 vape pens, different cartomizer configurations, and different strains and brands of *Cannabis* oil is critical to physicians and their patients.

So, for example, these variables may be tested using the described system. Further, the described system may be used to capture vapor generated by medical devices to assess the consistency of concentration of medicine. For current technology, it is difficult to perform these assessments using the small volume of aerosolized/vaporized medication generated by a single draw, thus, the present system enables aggregation of the output of ten devices, which can then be analyzed and divided by ten to obtain an average medication output quantification and concentration assessment. Each of the plurality of positive pressure inhalers 3302 can be actuated sequentially, or all at once.

As used herein, a vapor is a substance in the gas phase at a temperature lower than its critical temperature, which means that the vapor can be condensed to a liquid by increasing the pressure on it without reducing the temperature. A vapor is different from an aerosol. An aerosol is a suspension of tiny particles of liquid, solid, or both within a gas. Throughout this disclosure, the terms "vapor/aerosol" or "vaporized/aerosolized medication" are used to refer to a medication that can be delivered to the lungs of a patient as a vapor or an aerosol (with liquid particles, solid particles, or both) and is intended to have the broadest reasonable interpretation to a person of ordinary skill in the art, unless further modified or restricted in the claims.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments disclosed.

Insofar as the description above discloses any additional subject matter that is not within the scope of the claims below, the inventions are not dedicated to the public and the right to file one or more applications to claim such additional inventions is reserved.

What is claimed is:

1. A positive pressure inhaler for delivery of inhalable medication to a patient comprising:

a pump chamber of known volume, including interior side walls;

a piston that engages the interior side walls of the pump chamber;

an inflow valve operably connected to the pump chamber;

an outflow valve operably connected to the pump chamber;

a patient delivery port operably connected to the outflow valve;

wherein the piston is configured to have a piston travel length that is equal to or less than a length of the pump chamber;

wherein the piston travel length defines a known delivery volume;

wherein the pump chamber and the piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation;

wherein the pump chamber and the piston are configured such that upon a second traversal of the piston through the pump chamber, the known volume of aerosolized/ vaporized medication for patient inhalation will be displaced by the second traversal of the piston and expelled through the outflow valve and through the patient delivery port for positive pressure inhalation by the patient;

an inflow port for introduction of the aerosolized/vaporized medication into the positive pressure inhaler, wherein the inflow port is operably connected to the inflow valve;

an inflow port valve comprising:
   an inflow valve primary inflow port;
   an inflow valve discretionary inflow port;
   an inflow port valve outflow port; and
   an inflow port valve member;

wherein the inflow valve outflow port is operably connected to the pump chamber inflow valve;

wherein the inflow valve primary inflow port is operably connected to the inflow port;

wherein the inflow port valve member is configured such that actuation of the inflow port valve member switches between a first position that enables flow from the inflow valve primary inflow port, and a second position that enables flow from the inflow valve discretionary inflow port;

wherein the inflow port is configured to accept insertion of a medical device for generation of aerosolized/vaporized medication;

wherein the inflow port is further configured to create a generally airtight seal between the inflow port and the outflow of the medical device for generation;

whereby the inflow port valve member may be actuated to the first position to enable flow from the inflow valve primary inflow port so that a first defined volume of aerosolized/vaporized medication to be generated by the medical device for generation will be introduced into the pump chamber by negative pressure;

and further whereby the inflow port valve member may be actuated to the second position to enable flow from the inflow valve discretionary inflow port.

2. The positive pressure inhaler of claim 1 wherein the inflow valve discretionary inflow port is operably connected to an opening to the atmosphere, so that a first defined volume of air may be introduced into the pump chamber by negative pressure to dilute the first defined volume of aerosolized/vaporized medication.

3. The positive pressure inhaler of claim 1 wherein the inflow valve discretionary inflow port is operably connected to a discretionary medical device, so that a second volume of a gas may be introduced into the pump chamber by negative pressure to dilute the first defined volume of aerosolized/vaporized medication.

4. The positive pressure inhaler of claim 3 wherein the second volume of gas comprises a therapeutic gas.

5. The positive pressure inhaler of claim 4 wherein the therapeutic gas comprises pure oxygen.

6. The positive pressure inhaler of claim 3 wherein the second volume of gas is a second aerosolized/vaporized medication.

7. The positive pressure inhaler of claim 6 wherein the second aerosolized/vaporized medication is lidocaine.

8. The positive pressure inhaler of claim 1 comprising:
wherein the medical device for generation is a pMDI and the inflow port is configured to accept insertion of a mouthpiece of the pMDI; and wherein the inflow port is further configured to create a generally airtight seal between the inflow port and the mouthpiece upon insertion of the pMDI.

9. The positive pressure inhaler of claim 1 comprising:
wherein the medical device for generation is a 510 thread vaporizer and the inflow port is configured to accept insertion of a mouthpiece of the 510 thread vaporizer; and wherein the inflow port is further configured to create a generally airtight seal between the inflow port and the mouthpiece upon insertion of the 510 thread vaporizer.

10. The positive pressure inhaler of claim 9 further comprising:
a 510 thread vaporizer rest;

wherein the 510 thread vaporizer rest is configured to secure a battery section of the 510 thread vaporizer such that upon insertion of the mouthpiece of the 510 thread vaporizer into the inflow port and the insertion of the battery section into the 510 thread vaporizer rest, the weight of the battery section is supported to maintain the generally airtight seal between the inflow port and the mouthpiece.

11. The positive pressure inhaler of claim 1 wherein the inflow port valve is a ball valve.

12. The positive pressure inhaler of claim 1 further comprising:
a holding chamber comprising a chamber and an inflow port configured to accept insertion of a medical device for generation of aerosolized/vaporized medication;

wherein the inflow port is further configured to create a generally airtight seal between the inflow port and an outflow port of the medical device for generation; and wherein the holding chamber is operably connected to the inflow valve.

13. The positive pressure inhaler of claim 12 wherein the medical device for generation is a pMDI and the outflow port of the medical device for generation is a mouthpiece of the pMDI.

14. The positive pressure inhaler of claim 12 wherein the medical device for generation is a 510 thread vaporizer and the outflow port of the medical device for generation is a mouthpiece of the 510 thread vaporizer.

15. The positive pressure inhaler of claim 1 further comprising a transparent viewing pane that enables viewing of the pump chamber to verify that it contains aerosolized/vaporized medication.

16. The positive pressure inhaler of claim 1 further comprising a motor operably connected to the piston, wherein the motor is configured to drive the first traversal of the piston.

17. The positive pressure inhaler of claim 1 further comprising a flow rate indicator.

18. The positive pressure inhaler of claim 1 wherein the flow rate indicator indicates a rate of travel of the piston.

19. The positive pressure inhaler of claim 1 further comprising a volume indicator, wherein the volume indicator indicates a distance that the piston has travelled during the first traversal the piston.

20. The positive pressure inhaler of claim 1 further comprising an adjustable stop to control an amount of aerosolized/vaporized medication drawn into pump chamber.

21. The positive pressure inhaler of claim 20 further comprising a notification device to notify a user when a defined portion of the pump chamber has been filled with aerosolized/vaporized medication.

22. The positive pressure inhaler of claim 21 wherein the notification device emits a sound.

23. The positive pressure inhaler of claim 21 wherein the notification device emits a light.

24. The positive pressure inhaler of claim 1 wherein the patient delivery port comprises a patient mouthpiece.

25. The positive pressure inhaler of claim 24 wherein the patient mouthpiece is removable.

26. The positive pressure inhaler of claim 1 further comprising a one-way anti-blowback valve to prevent the patient from pushing aerosolized/vaporized medication back through the patient delivery port and into the pump chamber.

27. A positive pressure inhaler for delivery of inhalable medication to a patient comprising:
- a pump chamber of known volume, including interior side walls;
- a piston that engages the interior side walls of the pump chamber;
- an inflow valve operably connected to the pump chamber;
- an outflow valve operably connected to the pump chamber;
- a patient delivery port operably connected to the outflow valve;
- wherein the piston is configured to have a piston travel length that is equal to or less than the length of the pump chamber;
- wherein the piston travel length defines a known delivery volume;
- wherein the pump chamber and the piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation;
- wherein the pump chamber and the piston are configured such that upon a second traversal of the piston through the pump chamber, the known volume of aerosolized/vaporized medication for patient inhalation will be displaced by the second traversal of the piston and expelled through the outflow valve and through the patient delivery port for positive pressure inhalation by the patient;
- an inflow port for introduction of the aerosolized/vaporized medication into the positive pressure inhaler, wherein the inflow port is operably connected to the inflow valve;
- wherein the piston operably divides the pump chamber into a first section and a second section;
- wherein the inflow valve is operably connected to the first section of the pump chamber;
- wherein the outflow valve is operably connected to the first section of the pump chamber;
- a secondary inflow valve operably connected to the second section of the pump chamber;
- a secondary outflow valve operably connected to the second section of the pump chamber and the patient delivery port;
- wherein the pump chamber, the piston, the inflow valve, the outflow valve, the secondary inflow valve and the secondary outflow valve are configured such that the positive pressure inhaler has a double-action such that upon the second traversal of the piston through the pump chamber and while the aerosolized/vaporized medication is displaced from the first section of the pump chamber and through the patient delivery port, a second dose of aerosolized/vaporized medication will be drawn through the secondary inflow valve into the second section of the pump chamber.

28. The positive pressure inhaler of claim 27 wherein, upon a third traversal of the piston through the pump chamber, and while the second dose of aerosolized/vaporized medication is displaced from the second section of the pump chamber and through the patient delivery port, a third dose of aerosolized/vaporized medication will be drawn through the inflow valve into the first section of the pump chamber.

29. An aerosol/vaporizer medication dosage testing system comprising:
- a plurality of positive pressure inhalers, each of which comprises:
- a pump chamber of known volume, including interior side walls;
- a piston that engages the interior side walls of the pump chamber;
- an inflow valve operably connected to the pump chamber;
- an outflow valve operably connected to the pump chamber;
- a patient delivery port operably connected to the outflow valve;
- wherein the piston is configured to have a piston travel length that is equal to or less than a length of the pump chamber;
- wherein the piston travel length defines a known delivery volume;
- wherein the pump chamber and the piston are configured such that upon a first traversal of the piston through the pump chamber, negative pressure will be generated, such that aerosolized/vaporized medication will be drawn into the pump chamber through the inflow valve, creating a known volume of aerosolized/vaporized medication for patient inhalation;
- wherein the pump chamber and the piston are configured such that upon a second traversal of the piston through the pump chamber, the known volume of aerosolized/vaporized medication for patient inhalation will be displaced by the second traversal of the piston and expelled through the outflow valve and through the patient delivery port for positive pressure inhalation by the patient;
- a volumetric testbed comprising:
- a support table on which the plurality of positive pressure inhalers are mounted;
- a receiver valve;
- wherein the receiver valve is in airtight communication with each of the patient delivery ports of each of the plurality of positive pressure inhalers; and
- a capture vessel;
- wherein the receiver valve is in airtight communication with the capture vessel, configured such that, upon traversal of each of the respective pistons of each of the plurality of positive pressure inhalers, the respective aerosolized/vaporized medication of each of the positive pressure inhalers is displaced through the receiver valve and into the capture vessel.

30. The aerosol/vaporizer medication dosage testing system of claim 29 wherein the receiver valve is configured as a one-way valve biased toward the capture vessel.

31. The aerosol/vaporizer medication dosage testing system of claim 29 wherein the capture vessel comprises an inflatable balloon.

32. The aerosol/vaporizer medication dosage testing system of claim 29 wherein the capture vessel comprises a closure valve, such that when closed, the closure valve prevents escape of the respective aerosolized/vaporized medication of each of the positive pressure inhalers and further enables removal of the capture vessel from airtight communication with the receiver valve.

* * * * *